(12) United States Patent
Haydel et al.

(10) Patent No.: US 11,752,195 B2
(45) Date of Patent: Sep. 12, 2023

(54) **COMPOSITIONS AND METHODS OF USE OF SYNTHETIC PEPTIDES WITH *MYCOBACTERIUM ABSCESSUS* INHIBITORY ACTIVITY**

(71) Applicants: Shelley Haydel, Mesa, AZ (US); Chris Diehnelt, Chandler, AZ (US)

(72) Inventors: Shelley Haydel, Mesa, AZ (US); Chris Diehnelt, Chandler, AZ (US)

(73) Assignee: Arizona Board of Regents on Behalf of Arizona State Univeristy, Scottsdale, AZ (US)

( * ) Notice: Subject to any disclaimer, the term of this patent is extended or adjusted under 35 U.S.C. 154(b) by 0 days.

(21) Appl. No.: 17/722,081

(22) Filed: Apr. 15, 2022

(65) Prior Publication Data

US 2022/0339247 A1    Oct. 27, 2022

Related U.S. Application Data

(60) Provisional application No. 63/175,263, filed on Apr. 15, 2021.

(51) Int. Cl.
*A61P 31/04* (2006.01)
*A61K 47/18* (2017.01)
*A61K 38/17* (2006.01)
*C12Q 1/18* (2006.01)

(52) U.S. Cl.
CPC ........ *A61K 38/1729* (2013.01); *A61K 47/183* (2013.01); *A61P 31/04* (2018.01); *C12Q 1/18* (2013.01)

(58) Field of Classification Search
CPC ... A61K 38/1729; A61K 47/183; A61P 31/04; C12Q 1/18
See application file for complete search history.

(56) References Cited

PUBLICATIONS

Legutki JB, Zhao Z-G, Greving M, Woodbury N, Johnston SA, Stafford P. 2014. Scalable high-density peptide arrays for comprehensive health monitoring. Nat Commun 5.

Lei J, Sun L, Huang S, Zhu C, Li P, He J, Mackey V, Coy DH, He Q. The antimicrobial peptides and their potential clinical applications. Am J Transl Res. 2019;11(7):3919-31. Epub Aug. 10, 2019. PubMed PMID: 31396309; PMCID: PMC6684887.

Lister T, editor. Next-generation polymyxin analog SRP206. ASM Microbe; Jun. 21, 2019, 2019; San Francisco, CA: American Society for Microbiology.

Mahlapuu M, Hakansoon J, Ringstad L, Bjorn C. Antimicrobial Peptides: An Emerging Category of Therapeutic Agents. Front Cell Infect Microbiol 6: 194.

(Continued)

*Primary Examiner* — Kevin S Orwig
*Assistant Examiner* — John Michael Cronin
(74) *Attorney, Agent, or Firm* — BOOTH UDALL FULLER, PLC

(57) ABSTRACT

Synthetic antimicrobial peptides, compositions comprising thereof, and methods of use for modulating one or more symptoms of an infection in a subject are disclosed. In some aspects, the infection is caused by mycobacteria, for example, a nontuberculous *mycobacterium* such as *Mycobacterium abscessus*. In other aspects, the infection is caused by *Escherichia coli*, *Pseudomonas aeruginosa*, or methicillin-resistant *Staphylococcus aureus* (MRSA). Also disclosed are methods of identifying synthetic antimicrobial peptides against a pathogen with no known effective treatment using a library of synthetic peptides.

14 Claims, 9 Drawing Sheets

Specification includes a Sequence Listing.

(56) References Cited

PUBLICATIONS

Maurer FP, Ruegger V, Ritter C, Bloemberg GV, Bottger EC. 2012. Acquisition of clarithromycin resistance mutation in the 23S rRNA gene of *Mycobacterium abscessus* in the presence of inducible erm(41). J Antimicrob Chemother 67(11):2606-2611.

Medjahed H, Gaillard JL, Reyrat JM. 2010. *Mycobacterium abscessus*: a new player in the mycobacterial field. Trends Microbiol 18(3): 1 17-123.

Medjahed H, Reyrat JM. 2009. Construction of *Mycobacterium abscessus* defined glycopeptidolipid mutants: comparison of genetic tools. Appl Environ Microbiol 75:1331-1338.

Mo M, Yang Y, Zhang F, Jing W, Iriya R, Popovich J, Wang S, Grys T, Haydel SE, Tao N. Rapid Antimicrobial Susceptibility Testing of Patient Urine Samples Using Large Volume Free-Solution Light Scattering Microscopy. Anal Chem. 2019;91(15):10164-71. Epub Jul. 10, 2019. doi: 10.1021/acs.analchem.9b02174. PubMed PMID: 31251566; PMCID: PMC7003966.

Naafs MA. The Antimicrobial Peptides: Ready for Clinical Trials? Biomedical Journal of Scientific & Technical Research. 2018;7(4):6038-42.

Namkoong H, Kurashima A, Morimoto K, Hoshino Y, Hasegawa N, Ato M, Mitarai S. Epidemiology of Pulmonary Nontuberculous Mycobacterial Disease, Japan. Emerg Infect Dis. 2016;22(6):1116-7. doi: 10.3201/eid2206.151086. PubMed PMID: 27191735; PMCID: PMC4880076.

Nessar R, Cambau E, Reyrat JM, Murray A, Gicquel B. *Mycobacterium abscessus*: a new antibiotic nightmare. J Antimicrob Chemother. 2012;67(4):810-8. Epub Jan. 30, 2012. doi: 10.1093/jac/dkr578. PubMed PMID: 22290346.

Nessar R, Reyrat JM, Davidson LB, Byrd TF. Deletion of the mmpL4b gene in the *Mycobacterium abscessus* glycopeptidolipid biosynthetic pathway results in loss of surface colonization capability, but enhanced ability to replicate in human macrophages and stimulate their innate immune response. Microbiology. 2011;157(Pt4):1187-95. doi: 10.1099/mic.0.046557-0. PubMed PMID: 21292749.

Noll H, Block H, Asselineau J, Lederer R. 1956. The chemical structure of the cord factor of *Mycobacterium tuberculosis*. Biochimica et Biophysica Acta 20:299-309.

Oliva R et al. 2018. Exploring the role of unnatural amino acids in antimicrobial peptides. Sci Rep 8:8888.

Olivier KN, et al. 2002. Nontuberculous Mycobacteria: Multicenter Prevalence Study in cystic Fibrosis. Am J Respir Crit Care Med 167(6):828-834.

Papo N, Oren Z, Pag U, Sahl HG, Shai Y. The consequence of sequence alteration of an amphipathic alpha-helical antimicrobial peptide and its diastereomers. J Biol Chem. 2002;277(37):33913-21. Epub Jul. 12, 2002. doi: 10.1074/jbc.M204928200. PubMed PMID: 12110678.

Pasupuleti M, Schmidtchen A, Malmsten M. Antimicrobial peptides: key components of the innate immune system. Crit Rev Biotechnol. 2012;32(2):143-71. Epub Nov. 15, 2011. doi: 10.3109/07388551.2011.594423. PubMed PMID: 22074402.

Pawlik A et al. 2013. Identification and Characterization of the Genetic Changes Responsible for the Characteristic Smooth-to-Rough Morphotype Alterations of Clinically Persistent Mycobacterium abscessus. Mol Microbiol 90(3):612-629.

Pfalzgraff A, Brandenburg K, Weindl G. Antimicrobial Peptides and Their Therapeutic Potential for Bacterial Skin Infections and Wounds. Front Pharmacol. 2018;9:281. Epub Apr. 13, 2018. doi: 10.3389/fphar.2018.00281. PubMed PMID: 29643807; PMCID: PMC5882822.

Ragle BE, Wardenburg JB. 2009. Anti-Alpha-Hemolysin Monoclonal Antibodies Mediate Protection against *Staphylococcus aureus* Pneumonia Infection and Immunity 77:2712-2718.

Recht J, Martinez A, Torello S, Kolter R. 2000. Genetic analysis of sliding motility in *Mycobacterium smegmatis*. J Bacteriol 182:4348-4351.

Rottman M, Catherinot E, Hochedez P, Emile JF, Casanova JL, Gaillard IL, Soudais C. 2007. Importance of T cells, gamma interferon, and tumor necrosis factor in immune control of the rapid grower *Mycobacterium abscessus* in C57BL/6 mice. Infect Immun 75:5898-5907.

Roux AL et al. 2016. The Distinct Fate of Smooth and Rough *Mycobacterium abscessus* Variants inside Macrophages. Open Biol 6(11):160-185.

Ruger K, Hampel A, Billig S, Rucker N, Suerbaum S, Bange FC. 2014. Characterization of rough and smooth morphotypes of *Mycobacterium abscessus* isolates from clinical specimens. J Clin Microbiol 52:244 250.

Schorey JS, Sweet L. 2008. The mycobacterial glycopeptidolipids: structure, function, and their role in pathogenesis. Glycobio 18(11):832-841.

Shen Y, Maupetit J, Derreumaux P, Tufféry P. 2014. Improved PEP-FOLD approach for peptide and miniprotein structure prediction. J Chem Theor Comput 10:4745-4758.

Sonden B, Kocincova D, Deshayes C, Euphrasie D, Rhayat L, Laval F, Frehel C, Daffe M, Etienne G, Reyrat JM. 2005. Gap, a mycobacterial specific integral membrane protein, is required for glycolipid transport to the cell surface. Mol Microbiol 58:426-440.

Starr, C. G., & Wimley, W. C. (2017). Antimicrobial peptides are degraded by the cytosolic proteases of human erythrocytes. Biochimica et biophysica acta. Biomembranes, 1859(12), 2319-2326. https://doi.org/10.1016/j.bbamem.2017.09.008.

Strnad L, Winthrop KL. Treatment of *Mycobacterium abscessus* Complex. Semin Respir Crit Care Med. 2018;39(3):362-76. Epub Aug. 2, 2018. doi: 10.1055/s-0038-1651494. PubMed PMID: 30071551.

Thévenet P, Shen Y, Maupetit J, Guyon F, Derreumaux P, Tufféry P. 2012. PEP-FOLD: an updated de novo structure prediction server for both linear and disulfide bonded cyclic peptides. Nucleic Acids Res 40:W288-293.

Trentini MM, das Neves RC, Santos BP, DaSilva RA, de Souza AC, Mortari MR, Schwartz EF, Kipnis A, Junqueira-Kipnis AP. Non-disulfide-Bridge Peptide 5.5 from the Scorpion *Hadrurus gertschi* Inhibits the Growth of *Mycobacterium abscessus* subsp. massiliense. Front Microbiol. 2017;8:273. doi: 10.3389/fmicb.2017.00273. PubMed PMID: 28275372; PMCID: PMC5319999.

Vinnard C, Longworth S, Mezochow A, Patrawalla A, Kreiswirth BN, Hamilton K. Deaths Related to Nontuberculous Mycobacterial Infections in the United States, 1999-2014. Ann Am Thorac Soc. 2016;13(11):1951-5. doi: 10.1513/AnnalsATS.201606-474BC. PubMed PMID: 27607541; PMCID: PMC5122483.

Wagner D, Young LS. Nontuberculous mycobacterial infections: a clinical review. Infection. 2004;32(5):257-70. PubMed PMID: 15624889.

Wang CK, Craik DJ. Designing macrocyclic disulfide-rich peptides for biotechnological applications. Nat Chem Biol. 2018;14(5):417-27. Epub Apr. 18, 2018. doi: 10.1038/s41589-018-0039-y. PubMed PMID: 29662187.

Wang P, Nan YH, Yang ST, Kang SW, Kim Y, Park IS, Hahm KS, Shin SY. Cell selectivity and anti-inflammatory activity of a Leu/Lys-rich alpha-helical model antimicrobial peptide and its diastereomeric peptides. Peptides. 2010;31(7):1251-61. Epub Apr. 7, 2010. doi: 10.1016/j.peptides.2010.03.032. PubMed PMID: 20363271.

Whang J, Back YW, Lee KI, Fujiwara N, Paik S, Choi CH, Park JK, Kim HJ. *Mycobacterium abscessus* glycopeptidolipids inhibit macrophage apoptosis and bacterial spreading by targeting mitochondrial cyclophilin D. Cell Death Dis. 2017;8(8):e3012. Epub Aug. 24, 2017. doi: 10.1038/cddis.2017.420. PubMed PMID: 28837151; PMCID: PMC5596598.

Yeaman MR, Yount NY. Mechanisms of antimicrobial peptide action and resistance. Pharmacol Rev. 2003;55(1):27-55. Epub Mar. 5, 2003. doi: 10.1124/pr.55.1.2. PubMed PMID: 12615953.

Zhang F, Jiang J, McBride M, Yang Y, Mo M, Iriya R, Peterman J, Jing W, Grys T, Haydel SE, Tao N, Wang S. Direct Antimicrobial Susceptibility Testing on Clinical Urine Samples by Optical Tracking of Single Cell Division Events. Small. 2020;16(52):e2004148. Epub Nov. 30, 2020. doi: 10.1002/smll.202004148. PubMed PMID: 33252191; PMCID: PMC7770081.

Zhang F, Jiang J, McBride M, Zhou X, Yang Y, Mo M, Peterman J, Grys T, Haydel SE, Tao N, Wang S. Rapid Antimicrobial Suscep-

(56) References Cited

PUBLICATIONS tibility Testing on Clinical Urine Samples by Video-Based Object Scattering Intensity Detection. Anal Chem. 2021;93(18):7011-21. Epub Apr. 28, 2021. doi: 10.1021/acs.analchem.1c00019. PubMed PMID: 33909404; PMCID: PMC8152505.

Zhang L, Parente J, Harris SM, Woods DE, Hancock RE, Falla TJ. Antimicrobial peptide therapeutics for cystic fibrosis. Antimicrob Agents Chemother. 2005;49(7):2921-7. doi: 10.1128/AAC.49.7. 2921-2927.2005. PubMed PMID 15980369; PMCID: PMC1168697.

Zhao Y, Zhang M, Qui S, Wang J, Peng J, Zhao P, Zhu R, Wang H, Li Y,Wwang K, Yan W, Wang R. 2016. Antimicrobial activity and stability of the D-amino acid substituted derivatives of antimicrobial peptide polybia-MPI. AMB Express 6:122.

Adiemian J. Olivier KN. Seitz AE. Holland SM. Prevots DR. 2012. Prevalence of nontuberculous mycobacterial lung disease in U.S Medicare beneficiaries. Am J Respir Cir Care Med 185(8):881-886.

Aminov RI. A brief history of the antibiotic era: lessons learned and challenges for the future. Front Microbiol. 2010;1:134. Epub Dec. 8, 2010. doi: 10.3389/fmicb.2010.00134. PubMed PMID: 21687759; PMCID: PMC3109405.

Bahar AA, Ren D. Antimicrobial peptides. Pharmaceuticals (Basel). 2013;6(12):1543-75. Epub Nov. 30, 2013. doi: 10.3390/ph6121543. PubMed PMID: 24287494; PMCID: PMC3873676.

Ballarino GJ, Olivier KN, Claypool RJ, Holland SM, Prevots DR. Pulmonary nontuberculous mycobacterial infections: antibiotic treatment and associated costs. Respir Med. 2009;103(10):1448-55. doi: 10.1016/j.rmed.2009.04.026. PubMed PMID: 19467851; PMCID: PMC2739259.

Barrow W W. 2001. Treatment of Mycobacterial Infections. Rev Sci Tech 20(1):55-70.

Bernut A, Herrmann JL, Kissa K, Dubremetz JF, Gaillard JL, Lutfalla G, Kremer L. *Mycobacterium abscessus* cording prevents phagocytosis and promotes abscess formation. Proc Natl Acad Sci U S A. 2014;111(10):E943-52. Epub Feb. 24, 2014. doi: 10.1073/pnas.1321390111. PubMed PMID: 24567393; PMCID: PMC3956181.

Bernut A, Viljoen A, Dupont C, Sapriel G, Blaise M, Bouchier C, Brosch R, de Chastellier C, Herrmann JL, Kremer L. Insights into the smooth-to-rough transitioning in *Mycobacterium bolletii* unravels a functional Tyr residue conserved in all mycobacterial MmpL family members. Mol Microbiol. 2016;99(5):866-83. doi: 10.1111/mmi.13283. PubMed PMID: 26585558.

Bryant JM et al. 2013. Whole-Genome Sequencing to Identify Transmission of *Mycobacterium abscessus* between Patients with Cystic Fibrosis: A Retrospective Cohort Study. Lancet 381: 1551-1560.

Byrd TF, Lyons CR. 1999. Preliminary characterization of a *Mycobacterium abscessus* mutant in human and murine models of infection. Infect Immun 67:4700-4707.

Cao H, Lai Y, Bougouffa S, Xu Z, Yan A. 2017. Comparative genome and transcriptome analysis reveals distinctive surface characteristics and unique physiological potentials of Pseudomonas aeruginosa ATCC 27853. BMC Genom 18:459.

Catherinot E, Roux AL, Macheras E, Hubert D, Matmar M, Dannhoffer L, Chinet T, Morand P, Poyart C, Heym B, Rottman M, Gaillard IL, Herrmann JL. 2009. Acute respiratory failure involving an R variant of *Mycobacterium abscessus*. J Clin Microbiol 47:271-274.

CDC. Antibiotic Resistance Threats in the United States, 2019. Atlanta, GA: U.S. Department of Health and Human Services, CDC; 2019.

CDC.Biggest threats and data. (Mar. 2, 2021). Retrieved Apr. 7, 2021, from https://www.cdc.gov/drugresistance/biggest-threats.html.

Dole ST. Who will develop new antibacterial agents? Philos Trans R Soc Lond B Biol Sci. 2014;369(1645):20130430. Epub May 12, 2014. doi: 10.1098/rstb.2013.0430. PubMed PMID: 24821916; PMCID: PMC4024223.

Cotter PD, Hill C, Ross RP. Bacterial lantibiotics: strategies to improve therapeutic potential. Curr Protein Pept Sci. 2005;6(1):61-75. Epub Jan. 11, 2005. doi: 10.2174/1389203053027584. PubMed PMID: 15638769.

Davidson LB, Nessar R, Kempaiah P, Perkins DJ, Byrd TF. 2011. *Mycobacterium abscessus* glycopeptidolipid prevents respiratory epithelial TLR2 signaling as measured by HbetaD2 gene expression and IL-8 release. PLoS One 6:e29148.

Deak D, Outterson K, Powers JH, Kesselheim AS. Progress in the Fight Against Multidrug-Resistant Bacteria? A Review of U.S. Food and Drug Administration—Approved Antibiotics, 2010-2015. Ann Intern Med. Sep. 2016 doi: 10.7326/M16-0291. Epub May 24, 2016.

Diehnelt C W. 2013. Peptide Array Based Discovery of Synthetic Antimicrobial Peptides. Frontiers in Microbiology 4.

Domenyuk V, Loskutov A, Johnston SA, Diehnelt CW. 2013. A Technology for Developing Synbodies with Antimicrobial Activity. PLOS ONE 8(1): e54162.

Esther CR, Esserman DA, Gilligan P, Kerr A, Noon PG. 2010. Chronic *Mycobacterium abscessus* infection and lung function decline in cystic fibrosis. J Cyst Fibros 9(2): 117-123.

Falkinham JO. 1996. Epidemiology of Infection by Nontuberculous Mycobacteria. Clin Microbiol Rev 9(2):177-215.

Fellner RC, Terryah ST, Tarran R. Inhaled protein/peptide-based therapies for respiratory disease. Mol Cell Pediatr. 2016;3(1):16. Epub Apr. 20, 2016. doi: 10.1186/s40348-016-0044-8. PubMed PMID: 27098663; PMCID: PMC4839019.

Fernades HP, Cesar CL, Barjas-Castro ML. 2011. Electrical properties of the red blood cell membrane and immunohematological investigation. Rev Bras Hemtol Hemoter 33(4):297-301.

Field SK, Cowie RL. 2005. Lung Disease Due to the More Common Nontuberculous Mycobacteria. Chest 129(6): 1653-1672.

Greber KE, Dawgul M. Antimicrobial peptides under clinical trials. Curr Top Med Chem. 2017;17(5):620-8. Epub Jul. 15, 2016. PubMed PMID: 27411322.

Greendyke R and Byrd T F. 2008. Differential Antibiotic Susceptibility of *Mycobacterium abscessus* Variants in Biofilms and Macrophages Compared to that of Planktonic Bacteria. Antimicrob Agents Chemother 52(6):2019-2026.

Griffith DE, Aksamit T, Brown-Elliott BA, Catanzaro A, Daley C, Gordin F, Holland SM, Horsburgh R, Huitt G, Iademarco MF, Iseman M, Olivier K, Ruoss S, von Reyn CF, Wallace RJ, Jr., Winthrop K, Subcommittee ATSMD, American Thoracic S, Infectious Disease Society of A. An official ATS/IDSA statement: diagnosis, treatment, and prevention of nontuberculous mycobacterial diseases. Am J Respir Crit Care Med. 2007;175(4):367-416. doi: 10.1164/rccm.200604-571ST. PubMed PMID: 17277290.

Grosser L, Heang K, Teague J, Warn P, Corbett D, Dawson MJ, Rubio A. Poster-139: In Vivo Efficacy of SPR206 in Murine Lung and Thigh Infection Models Caused by Multidrug Resistant Pathogens *Pseudomonas aeruginosa* and *Acinetobacter baumanii*. ASM ESCMID; Lisbon, Portugal2018.

Hale JD, Hancock RE. Alternative mechanisms of action of cationic antimicrobial peptides on bacteria. Expert Rev Anti Infect Ther. 2007;5(6):951-9. doi: 10.1586/14787210.5.6.951. PubMed PMID: 18039080.

Hancock RE, Sahl HG. 2006. Antimicrobial and host-defense peptides as new anti-infective therapeutic strategies. Mature Biotechnol.

Howard ST, Rhoades E, Recht J, Pang X, Alsup A, Koiter R, Lyons CR, Byrd TF. 2006. Spontaneous reversion of *Mycobacterium abscessus* from a smooth to a rough morphotype is associated with reduced expression of glycopeptidolipid and reacquisition of an invasive phenotype. Microbiol 152:1581-1590.

Jackson M. 2014. The Mycobacterial Cell Envelope—Lipids. Cold Spring Harb Perspect Med 4(10):a021105.

Jarand J, Levin A, Zhang L, Huitt G, Mitchell JD, Daley CL. 2011. Clinical and Microbiologic Outcomes in Patients Receiving Treatment for *Mycobacterium abscessus* Pulmonary Disease. Clin Infect Dis 52(5):565-571.

Jeon K, Kwon OJ, Lee NY, Kim BJ, Kook YH, Lee SH, Park YK, Kim CK, Koh WJ. Antibiotic treatment of *Mycobacterium abscessus* lung disease: a retrospective analysis of 65 patients. Am J Respir Crit Care Med. 2009;180(9):896-902. doi: 10.1164/rccm.200905-0704OC. PubMed PMID: 19661243.

Jian He, Randal Eckert, Thanh Pharm, Maurice D. Simanian, Chuhong Hu, Daniel K. Yarbrough, Fengxia Qi, Maxwell H.

(56) References Cited

PUBLICATIONS

Anderson, Wenyuan Shi Antimicrobial Agents and Chemotherapy Mar. 2007, 51 (4) 1351-1358; DOI:10.1128/AAC.01270-06.

Johnson MM, Waller EA, Leventhal JP. Nontuberculous mycobacterial pulmonary disease. Curr Opin Pulm Med. 2008;14(3):203-10. doi: 10.1097/MCP.0b013e3282f9e650. PubMed PMID: 18427243.

Johnston SA, Domenyuk V, Gupta N, Batista MT, Lainson JC, Zhao Z-G, Lusk JF, Loskutov A, Cichacz Z, Stafford P, Legutki JB, Diehnelt CW. A Simple Platform for the Rapid Development of Antimicrobials. Scientific Reports. 2017;7(1):17610. doi: 10.1038/s41598-017-17941-7.

Jonsoon BE, Gilljam M, Lindblad A, Ridell M, Wold AE, Olsson CW. 2007. Molecular Epidemiology of *Mycobacterium abscessus*, with Focus on Cystic Fibrosis. J Clin Microbiol 45(5): 1497-1504.

Kalita A, Verma I, Khuller GK. Role of human neutrophil peptide-1 as a possible adjunct to antituberculosis chemotherapy. J Infect Dis. 2004;190(8):1476-80. doi: 10.1086/424463. PubMed PMID: 15378441.

Keener, A., Rauf, D., Dunleavy, B., Upham, B., Brownstein, J., Brown, J., & Worth, T. (n.d.). 7 scary Drug-Resistant Infections:Everyday Health. Retrieved Apr. 7, 2021, from https://www.everydayhealth.com/pictures/scary-drug-resistant-infections/.

Kendall BA and Winthrop KL. 2013. Update on the Epidemiology of Pulmonary Mycobacterial Infections. Semin Respir Crit Care Med 34(1):87-84.

Koh WJ, Jeong BH, Kim SY, Jeon K, Park KU, Jhun BW, Lee H, Park HY, Kim DH, Huh HJ, Ki CS, Lee NY, Kim HK, Choi YS, Kim J, Lee SH, Kim CK, Shin SJ, Daley CL, Kim H, Kwon OJ. Mycobacterial Characteristics and Treatment Outcomes in *Mycobacterium abscessus* Lung Disease. Clin Infect Dis. 2017;64(3):309-16. Epub Nov. 10, 2016. doi: 10.1093/cid/ciw724. PubMed PMID: 28011608.

Kokel A, Torok M. Recent Advances in the Development of Antimicrobial Peptides (AMPs): Attempts for Sustainable Medicine? Curr Med Chem. 2018;25(21):2503-19. Epub Jan. 24, 2018. doi: 10.2174/0929867325666180117142142. PubMed PMID: 29357788.

Kwok PC, Grabarek A, Chow MY, Lan Y, Li JC, Casettari L, Mason AJ, Lam JK. Inhalable spray-dried formulation of D-LAK antimicrobial peptides targeting tuberculosis. Int J Pharm. 2015;491(1-2):367-74. doi: 10.1016/j.jpharm.2015.07.001. PubMed PMID: 26151107.

Lainson JC, Daly SM, Triplett K, Johnston SA, Hall PR, Diehnelt CW. Synthetic Antibacterial Peptide Exhibits Synergy with Oxacillin against MRSA. ACS Medicinal Chemistry Letters. 2017;8(8):853-7. doi: 10.1021/acsmedchemlett.7b00200.

Lamiable A, Thevenet P, Rey J, Vavrusa M, Derreumaux P, Tuffery P. 2016. PEP-FOLD3: Faster de novo structure prediction for linear peptides in solution and in complex Nucleic Acids Res 44:W449 W454.

Landman D, Georgescu C, Martin DA, Quale J. Polymyxins revisited. Clin Microbiol Rev. 2008;21 (3):449-65. doi: 10.1128/CMR.00006-08. PubMed PMID: 18625681; PMCID: PMC2493081.

Lange CF, Hancock RE, Samuel J, Finlay WH. In vitro aerosol delivery and regional airway surface liquid concentralion of a liposomal cationic peptide. J Pharm Sci. 2001;90(10):1647-57. PubMed PMID: 11745723.

Lee MR, Sheng WH, Hung CC, Yu CJ, Lee LN, Hsueh PR. *Mycobacterium abscessus* complex infections in humans. Emerg Infect Dis. 2015;21(9):1638-46. doi: 10.3201/2109.141634. PubMed PMID: 26295364; PMCID: PMC4550155.

Lee TH, Hall KN, Aguilar MI. 2016. Antimicrobial Peptide Structure and Mechanism of Action: A Focus on the Role of Membrane Structure Curr Top Med Chem 16:25-39.

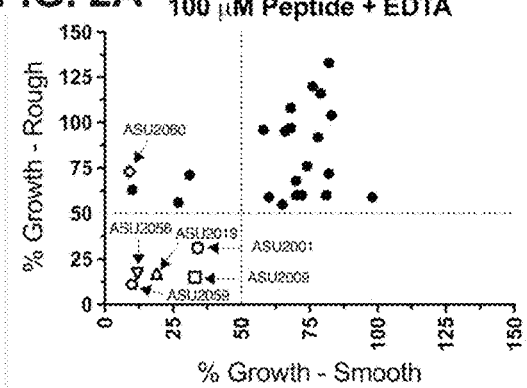
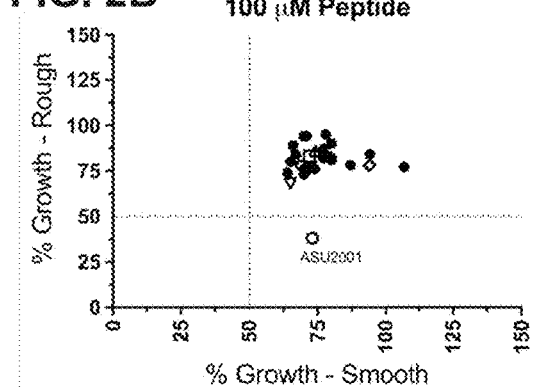
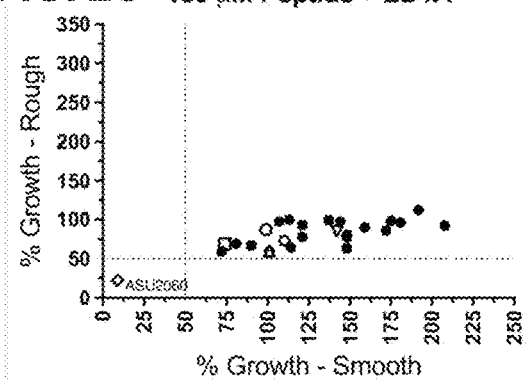
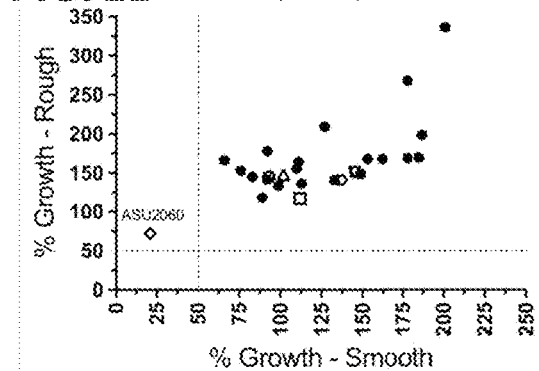
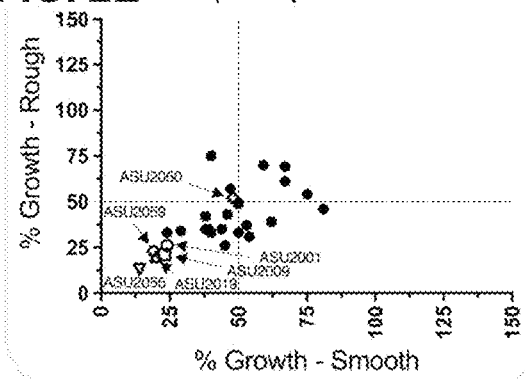
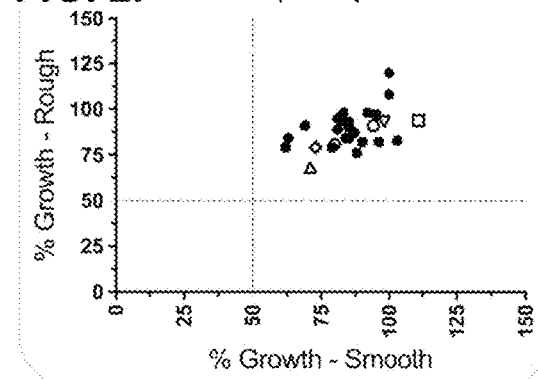

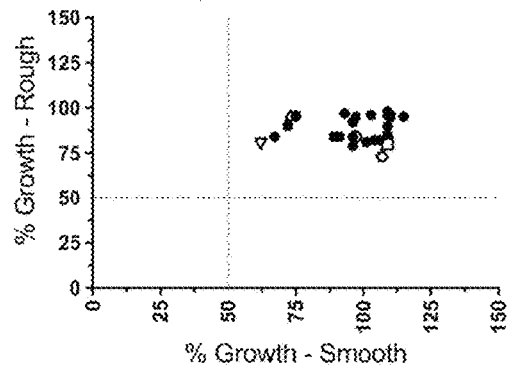
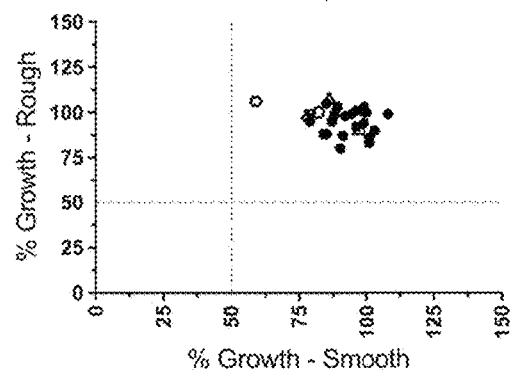
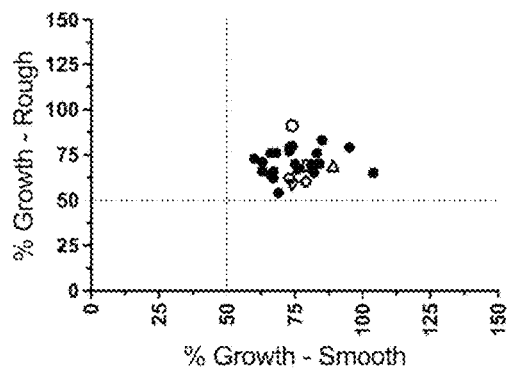
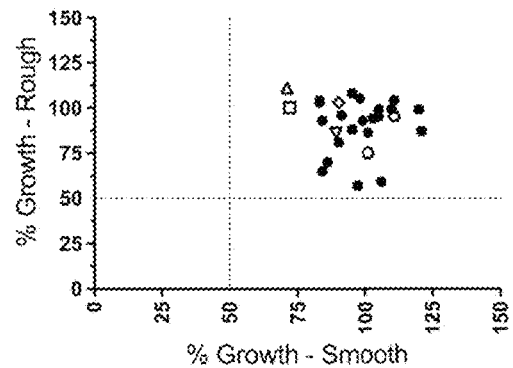
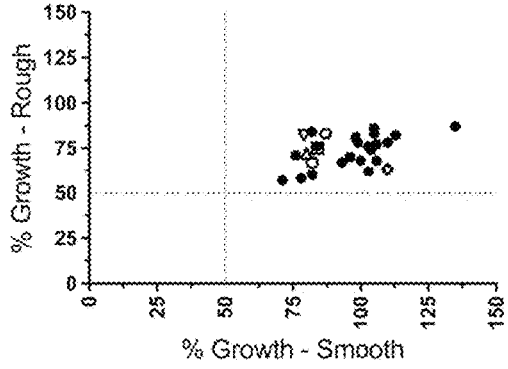
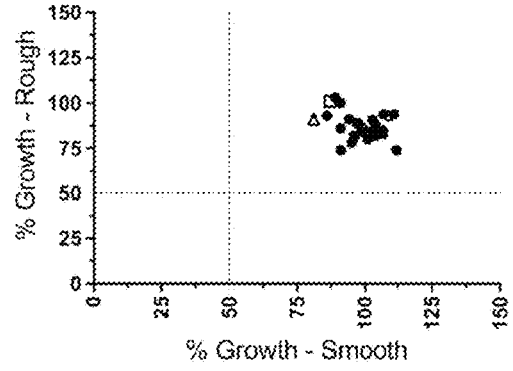

COMPOSITIONS AND METHODS OF USE OF SYNTHETIC PEPTIDES WITH *MYCOBACTERIUM ABSCESSUS* INHIBITORY ACTIVITY

CROSS-REFERENCE TO RELATED APPLICATIONS

This application claims the benefit of and priority to U.S. Provisional Application No. 63/175,263, filed Apr. 15, 2021, the contents of which are incorporated herein by reference in its entirety.

REFERENCE TO A SEQUENCE LISTING

The instant application contains a Sequence Listing which has been submitted electronically in ASCII format and is hereby incorporated by reference in its entirety. Said ASCII copy, created on Apr. 15, 2021, is named M210252L_PR1_f.TXT and is 3,761 bytes in size.

TECHNICAL FIELD

Embodiments herein relate to antimicrobial peptides (AMPs), and more specifically, to systems and methods of high-throughput screening to identify candidate AMPs, and to compositions of AMPs, AMPs, and methods of use thereof.

BACKGROUND

Antimicrobial resistance is a growing threat aggravated by the high cost and long duration of few viable treatment options available for resistant life-threatening infections. While resistant infection incidence is increasing, discoveries of novel targets for antimicrobials have declined since the 1970s. Even with new incentives offered in 2010 to spur antibiotic development and FDA approval, only 1 out of the 8 antimicrobials approved between 2010 and 2015 employed a novel mechanism of action. The rise in the number of antibiotic-resistant bacteria, due in part to the widespread use of antibiotics, has made it imperative to find alternative treatment options. Addressing antibiotic resistance will take a coordinated effort in antibiotic stewardship, diagnosis, and containment; however, the development of new therapeutics is critical to treat prevalent resistant pathogens.

Meanwhile, antimicrobial peptides (AMPs) are gaining prominence as alternative antimicrobials due to their specificity towards anionic bacterial membranes, rapid action, and limited development of resistance due to its action against the cell membrane. AMPs have been discovered in a diversity of organisms and have correspondingly diverse structures and specificities.

Antimicrobial peptides (AMPs) are cationic, amphipathic peptides that lyse bacteria via disruption of the cell membrane or inhibit bacterial growth via disruption of cell wall, DNA, RNA, and/or protein synthesis. The paucity of effective antibiotics has increased interest in AMPs due to their selectivity towards anionic bacterial cell membranes (instead of zwitterionic mammalian membranes), rapid action, and lack of resistance by primarily acting against the bacterial cell membrane. Without being bound to a theory, there are several proposed models that describe the mechanism by which AMPs interact with cell membranes. The "carpet model" suggests that the AMPs accumulate on the surface of the cell membrane, forming a carpet layer, which causes tension and ultimately disruption of the membrane. The "barrel stave model" proposes that the AMPs insert perpendicularly into the membrane bilayer and create a peptide-lined pore with the hydrophobic portion of the peptide interacting with the lipid core of the membrane and the hydrophilic portion of the peptide facing the interior of the pore. Lastly, the "toroidal-pore model" suggests that the insertion of the peptides perpendicular to the phospholipid bilayer causes the membrane to bend and form a pore lined by both lipid heads and peptides. While AMPs are naturally produced by the innate immune system, AMPs can be rationally designed based on their natural counterparts, optimized with amino acid substitutions, and synthesized.

Interest has increased in AMPs due to their selectivity towards anionic bacterial cell membranes, rapid action, and lack of developed resistance. As AMPs are increasingly considered as therapeutics, they are often designed and optimized with amino acid substitutions to be cationic and amphipathic so as to disrupt the cell membrane and either lyse the cell or inhibit growth via disruption of cell wall, DNA, RNA, and/or protein synthesis. However, novel AMP mechanisms may be discovered from screening random, synthetic peptides for antimicrobial activity. As the need for antimicrobials effective against resistant organisms intensifies, so must the pace of discovery methods. Discovery and development of novel AMPs will fill this gap in vital therapeutic options.

SUMMARY

Disclosed herein are synthetic antimicrobial peptides, compositions comprising thereof, and methods of use thereof for modulating one or more signs or symptoms of an infection in a subject. The synthetic antimicrobial peptides have a sequence set forth in SEQ ID NO: 1 (ASU2001), SEQ ID NO:2 (ASU2009), SEQ ID NO: 3 (ASU2019), SEQ ID NO: 4 (ASU2056), SEQ ID NO: 5 (ASU2059), and SEQ ID NO: 6 (ASU2060). Accordingly in some aspects, the antimicrobial composition disclosed herein comprises at least one peptide selected from the group consisting of: ASU2001, ASU2009, ASU2019, ASU2056, ASU2059, and ASU2060. In certain implementations, the composition further comprises a chelator that sequesters metal ions, for example, EDTA. In some embodiments, the composition also comprises an antibiotic.

The disclosed method of treating a bacterial infection in a subject comprises administering to the subject at least one peptide selected from the group consisting of: ASU2001, ASU2009, ASU2019, ASU2056, ASU2059, and ASU2060. In some aspects, the bacterial infection is caused by a bacterium selected from the group consisting of: *Escherichia coli*, *Pseudomonas aeruginosa*, methicillin-resistant *Staphylococcus aureus* (MRSA), and *Mycobacterium abscessus*. In certain implementations, the bacterial infection is a *mycobacterium* infection, for example, caused by a drug-resistant *mycobacterium*, such as *M. abscessus*. In some implementations, wherein the *mycobacterium* infection is caused by *M. abscessus* with a smooth morphotype, the method comprises administering to the subject at least one peptide is selected from ASU2056 and ASU2060 and administering to the subject a chelator that sequesters metal ions such as EDTA. In other implementations, wherein the *mycobacterium* infection is caused by *M. abscessus* with a rough morphotype, the method consists of administering to the subject ASU2001.

Also disclosed are methods of identifying synthetic antimicrobial peptides against a pathogen with no known effective treatment using a library of synthetic peptides. The method comprises generating a library of peptides having 15-18 amino acid residues in length using amino acids selected from the group consisting of: L-alanine, D-alanine, L-aspartic acid, D-aspartic acid, L-glutamic acid, D-glutamic acid, L-phenylalanine, D-phenylalanine, L-glycine, L-histidine, D-histidine, L-isoleucine, D-isoleucine, L-lysine, D-lysine, L-leucine, D-leucine, L-methionine, D-methionine, L-asparagine, D-asparagine, L-proline, D-proline, L-glutamine, D-glutamine, L-arginine, D-arginine, L-serine, D-serine, L-threonine, D-threonine, L-valine, D-valine, L-tryptophan, D-tryptophan, L-tyrosine, and D-tyrosine; and attaching the library of peptides on a silicon wafer, wherein the silicon wafer is coated with a photoresist and a photoacid generator to produce a peptide microarray. The method further comprises providing a suspension of bacterial cells, wherein the bacterial cells are fluorescently labeled; incubating the suspension of fluorescently labeled bacterial cells with the peptide microarray; and identifying peptides bound to the fluorescently labeled bacterial cells, wherein the peptides bound to the fluorescently labeled bacterial cells have a relative fluorescence unit that is at least 10 times the median signal of the fluorescence signal of the peptide microarray. Then, the peptides bound to the fluorescently labeled bacterial cells are administered to a culture of bacterial cells; and peptides that inhibit the growth of the culture of bacterial cells are then identified as synthetic antimicrobial peptides.

In particular implementations, the step of generating the library of peptides uses amino acids selected from the group consisting of: L-alanine, D-alanine, L-aspartic acid, L-glutamic acid, L-arginine, D-arginine, L-phenylalanine, L-glycine, L-histidine, L-isoleucine, L-lysine, D-lysine, L-leucine, D-leucine, L-methionine, L-asparagine, L-proline, L-glutamine, L-arginine, D-arginine, L-serine, L-threonine, L-valine, L-tryptophan, D-tryptophan, and L-tyrosine.

In some implementations, the step of administering the peptides bound to the fluorescently labeled bacterial cells to the culture of bacterial cells further comprises administering a chelator that sequesters metal ions to the culture of bacterial cells with peptides bound to the fluorescently labeled bacterial cells.

Where the method identifies synthetic antimicrobial peptides against a target bacterial species, the suspension of bacterial cells and the culture of bacterial cells consist essentially of the target bacterial species. In particular embodiments, the target bacterial species is M. abscessus.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIGS. 2A-2F illustrate, in accordance with certain embodiments, growth inhibition assays with 27 peptides that exhibited interaction with Mabs during the peptide microarray screening. FIGS. 2A and 2B depict minimum inhibitory concentration (MIC) assays with Mabs 19977S and Mabs 19977R were performed in M7H9 with peptide (100 µM) and EDTA (100 µM) or peptide (100 µM) alone. FIGS. 2C and 2D depict MIC assays with Mabs 19977S and Mabs 19977R were performed in CAMHB with peptide (100 µM) and EDTA (100 µM) or peptide (100 µM) alone. FIGS. 2E and 2F depict MIC assays with Mabs 19977S and Mabs 19977R were performed in MHB with peptide (100 µM) and EDTA (100 µM) or peptide (100 µM) alone. All experiments were incubated at 37° C. for 72 h. Peptides that reduced Mabs growth by ≥50% (hatched line), when compared to the growth control $OD_{600}$, were considered active. Panels highlight six peptides with consistent inhibitory activity against Mabs 199775 and Mabs 19977R in different media. ASU2001—open circles; ASU2009—open squares; ASU2019—open triangles; ASU2056—open inverted triangles; ASU2059—open hexagons; ASU2060—open diamonds. All experiments were performed in triplicate with the average of all three replicates plotted for each peptide.

FIGS. 3A-3F depict, in accordance with certain embodiments, the results of growth inhibition assays with the 27 peptides that interacted with Mabs during the peptide microarray screening. FIGS. 3A and 3B depict MIC assays with Mabs 19977S and Mabs 19977R were performed in M7H9 with peptide (10 µM) and EDTA (10 µM) or peptide (10 µM) alone. FIGS. 3C and 3D depict MIC assays with Mabs 19977S and Mabs 19977R were performed in CAMHB with peptide (10 µM) and EDTA (10 µM) or peptide (10 µM) alone. FIGS. 3E and 3F depict MIC assays with Mabs 19977S and Mabs 19977R were performed in MHB with peptide (10 µM) and EDTA (10 µM) or peptide (10 µM) alone. All experiments were incubated at 37° C. for 72 h. Peptides that reduced Mabs growth by ≥50% (hatched line), when compared to the growth control $OD_{600}$, were considered active. Panels highlight six peptides with consistent inhibitory activity against Mabs 19977S and 19977R in different media. ASU2001—open circles; ASU2009—open squares; ASU2019—open triangles; ASU2056—open inverted triangles; ASU2059—open hexagons; ASU2060—open diamonds. All experiments were performed in triplicate with the average of all three replicates plotted for each peptide.

DETAILED DESCRIPTION

Figure 1A:
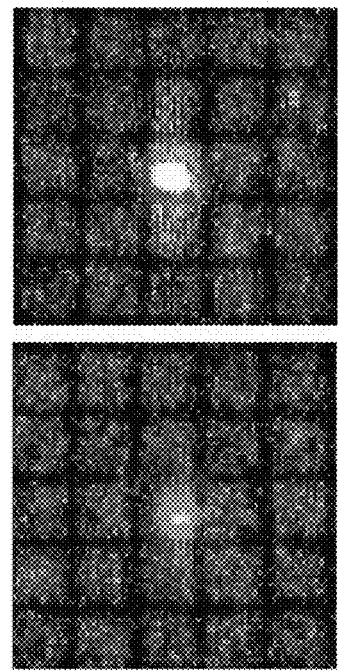
FIG. 1A depicts representative colonies of Mycobacterium abscessus (Mabs) ATCC19977S (left) and Mabs ATCC 19977R (right).

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical, electrical, or molecular contact with each other. "Coupled" may mean that two or more elements are in direct physical, electrical, or molecular contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Disclosed herein is a method of identifying synthetic peptides that can be used as an antimicrobial peptide (AMP) using a high-density peptide microarray consisting of over a hundred thousand random synthetic peptides. The method enables rapid screening of antimicrobial peptides against a target bacterium, for example, target bacteria that are pathogens without effective drug treatments such as *M. abscessus*. The method of identifying synthetic antimicrobial peptides comprises generating a library of peptides having 15-18 amino acid residues in length using L- and D-isomers of amino acids that make up protein found in the human body and then attaching the library of peptides on a silicon wafer, wherein the silicon wafer is coated with a photoresist and a photoacid generator to produce a peptide microarray. In certain implementations, the library of peptides are generated using amino acids selected from the group consisting of: L-alanine, D-alanine, L-aspartic acid, L-glutamic acid, L-arginine, D-arginine, L-phenylalanine, L-glycine, L-histidine, L-isoleucine, L-lysine, D-lysine, L-leucine, D-leucine, L-methionine, L-asparagine, L-proline, L-glutamine, L-arginine, D-arginine, L-serine, L-threonine, L-valine, L-tryptophan, D-tryptophan, and L-tyrosine. In particular embodiments, the library of peptides comprises peptides having 17 amino acid residues in length. In some aspects, the peptides are arranged in squares of 10 to 100 µm. In a certain implementation, the peptides are arranged in squares of 14 µm×14 µm.

Thus, in some aspects, disclosed herein is the production of high-density peptide microarrays of up to 330,000 random peptides using in situ synthesis, where photolithographic masks are used to illuminate discrete features on a silicon wafer coated with a photoresist and a photoacid generator.

The method further comprises providing a suspension of bacterial cells, wherein the bacterial cells are fluorescently labeled; incubating the suspension of fluorescently labeled bacterial cells with the peptide microarray; and identifying peptides bound to the fluorescently labeled bacterial cells. The peptides bound to the fluorescently labeled bacterial cells have a relative fluorescence unit that is at least 10 times the median signal of the fluorescence signal of the peptide microarray. The method still further comprises administering the peptides bound to the fluorescently labeled bacterial cells to a culture of bacterial cells and identifying peptides that inhibit the growth of the culture of bacterial cells as synthetic antimicrobial peptides. The suspension of bacterial cells and the culture of bacterial cells consist essentially of the target bacterial species for which the AMP property is sought. For example, where the method identifies synthetic AMP against *mycobacterium*, the suspension of bacterial cells and the culture of bacterial cells consist essentially of the *mycobacterium*. In some aspects, the target bacterial species is a nontuberculous *mycobacterium*, for example, *Mycobacterium abscessus* (*Mabs*). The *Mabs* may be the smooth morphotype or the rough morphotype.

The certain implementations, the method additionally comprises screening the peptides bound to the fluorescently labeled bacterial cells for antimicrobial properties against other bacterial species, wherein the other bacterial species is different than the target bacterial species, preferably in a different genus. For example, if the target species is *Mabs*, the other bacterial species is selected from the group consisting of *Escherichia coli, Pseudomonas aeruginosa*, and *Staphylococcus aureus* (for example, methicillin-resistant *S. aureus* (MRSA)).

In some aspects, the step of identifying peptides that inhibit the growth of the culture of bacterial cells as synthetic antimicrobial peptides may be performing an inhibitory assay and/or a bactericidal assay, for example, to determine the IC50 and/or the minimum inhibitory concentration (MIC) to inhibit bacteria growth or visible bacterial growth. Thus, disclosed herein are systems and methods for high-throughput identification and characterization of AMPs, and to compositions comprising AMPs.

The peptide microarray screening method described herein demonstrates several important features. The flexibility of the synthesis system enables production of diverse peptide libraries, including the use of less expansive D-amino acids and other non-canonical amino acids that offer improved protease stability or side chain diversity. Also important to this method's success, the peptide libraries have random sequences, enabling screening and discovery of new, atypical, or novel cellular interactions with unique mechanisms of action. Thirdly, the diverse phenotypic screening approach is adaptable for different microorganisms. Finally, the large number of replicate microarrays produced with the photolithographic synthetic approach, empower experimental screening designs with large numbers of replicates or screening conditions. These important features and flexibility enable the design of screens that produce viable hits, even for challenging organisms.

Also disclosed are synthetic peptides that have been identified to possess antimicrobial properties against a variety of microorganisms, including drug resistant Gram-negative and Gram-positive bacteria. These peptides have also been shown to have minimal toxicity. These synthetic AMPs comprise a sequence set forth in SEQ ID NO: 1 (ASU2001), SEQ ID NO:2 (ASU2009), SEQ ID NO: 3 (ASU2019), SEQ ID NO: 4 (ASU2056), SEQ ID NO: 5 (ASU2059), SEQ ID NO: 6 (ASU2060), SEQ ID NO: 7 (ASU2061), SEQ ID NO: 8 (ASU2062), or SEQ ID NO: 9 (ASU2070). As shown in these examples, these synthetic peptides inhibit the growth of *mycobacterium*, specifically drug-resistant *mycobacterium* like *Mabs*. These synthetic peptides also inhibit *E. coli, P. aeruginosa*, and *S. aureus* (in particular, MRSA). Accordingly, also disclosed are antimicrobial compositions comprising at least one of these synthetic AMPs and methods of using these synthetic AMPs for modulating one or more signs, symptoms, processes, molecules, cells and/or organisms (e.g., bacterium) associated with bacterial infection, for example in the use of treating a bacterial infection. In some aspects, the composition further comprises a chelator that sequesters metal ions, for example, EDTA. In other aspects, aspects, the composition further comprises an antibiotic.

The compositions may be useful, for example, against one or more of *M. abscessus, P. aeruginosa, S. aureus*, and *E. coli*. In some embodiments, the compositions are for treating a *mycobacterium* infection, for example, one caused by a drug-resistant *mycobacterium*. In particular, the compositions and methods treat a bacterial infection caused by *M. abscessus*.

Accordingly, methods of treating an infection in a subject are disclosed. Infections of interest that may be treated or prevented according to the subject methods include, but are not limited to, toxic shock syndrome, diphtheria, cholera, typhus, meningitis, whooping cough, botulism, tetanus, pyogenic infections, sinusitis, pneumonia, gingivitis, mucitis, folliculitis, cellulitis, acne and acne vulgaris, impetigo, osteomyelitis, endocarditis, ulcers, burns, dysentery, urinary tract infections, gastroenteritis, anthrax, Lyme disease, syphilis, rubella, septicemia, Buruli ulcer, mycetoma, chromoblastomycosis, vaginal candidiasis, tuberculosis, otitis media, eczema (atopic dermatitis), diabetic ulcers, impetigo, toenail fungus, venous ulcers, infected burns, infected wounds, infected ballistic wounds and plague; as well as primary, secondary, and opportunistic infections associated with, for example, trauma, surgery, endotracheal intubation, tracheostomy, and cystic fibrosis.

Also of interest are methods of treating gram-negative pathogens and multidrug-resistant gram-positive bacteria, such as community-acquired MRSA. Gram-negative bacteria of interest that may be targeted according to the subject methods include, but are not limited to, *Acinetobacter baumannii* and *P. aeruginosa*; Gram-positive bacteria, *S. aureus* and MRSA; and fungal strains, *Candida albicans, Candida parapsilosis, Candida krusei, Aspergillus fumigatus, Aspergillus flavus, Absidia corymbifera, Fusarium solani*, and *Mucor*.

In a particular embodiment, a method of treating a bacterial infection in a subject is disclosed, and the method comprises administering to the subject at least one peptide selected from the group consisting of: ASU2001 (SEQ ID NO: 1), ASU2009 (SEQ ID NO:2), ASU2019 (SEQ ID NO: 3), ASU2056 (SEQ ID NO: 4), ASU2059 (SEQ ID NO: 5), and ASU2060 (SEQ ID NO: 6). In some aspects, the methods comprise administering a variation of ASU2001, ASU2009, ASU2019, ASU2056, ASU2059, or ASU2060, for example, where the amino acid sequence differs by one to five amino acids as compared to ASU2001, ASU2009, ASU2019, ASU2056, ASU2059, or ASU2060. In some examples, the variations are not necessarily amino acid substitutions to different amino acid, but rather are differences in L-amino acid vs D-amino acid. For example, a D-amino acid in a peptide as disclosed herein may also be substituted with an L-amino acid, in embodiments, and vice versa.

The administering may be oral, sublingual, topical, subcutaneous, rectal, parenteral, intravenous, intramuscular, nasal, ocular, otic, and the like. It is herein contemplated that the administering may comprise administering a composition comprising one or more of ASU2001, ASU2009, ASU2019, ASU2056, ASU2059, ASU2060, ASU2061, ASU2062, and/or ASU2070 and/or one or more variations of ASU2001, ASU2009, ASU2019, ASU2056, ASU2059, ASU2060, ASU2061, ASU2062, and/or ASU2070. It is herein contemplated that such compositions, and hence such administering, may include one or more other therapeutic agents, or other pharmacological agents. As one example, the compositions as herein disclosed may include, in addition to one or more of ASU2001, ASU2009, ASU2019, ASU2056, ASU2059, ASU2060 ASU2061, ASU2062, and/or ASU2070 (and/or variations thereof), one or more antimicrobial agents (e.g., clarithromycin and the like).

A subject suitable for treatment with the disclosed antimicrobial composition may be identified by well-established indicators of risk for developing a disease or well-established hallmarks of an existing disease. For example, indicators of an infection include fever, pus, microorganism positive cultures, inflammation, and the like. Infections that may be treated with peptides provided by the present invention include without limitation those caused by or due to microorganisms, whether the infection is primary, secondary, opportunistic, or the like. Examples of microorganisms include bacteria (e.g., Gram-positive, Gram-negative), fungi, (e.g., yeast and molds), parasites (e.g., protozoans, nematodes, cestodes and trematodes), viruses (e.g., HIV, HSV, VSV), algae, and prions. Specific organisms in these classes are well known (see, for example, Davis et al., Microbiology, 3rd edition, Harper & Row, 1980, and Stanier et al., The Microbial World, 5th edition, Prentice Hall, 1986).

Mycobacterium Infection

Mycobacteria other than *Mycobacterium tuberculosis* and *Mycobacterium leprae* are referred to as nontuberculous mycobacteria (NTM) and are differentiated for the purpose of diagnosis and treatment. NTMs are ubiquitous, environmental inhabitants of water, soil, and dust and can cause pulmonary disease, lymphadenitis, skin, soft tissue, skeletal, and ocular infections, and bacteremia. Pulmonary infections caused by NTMs are an increasing public health problem in the US, where prevalence has risen 8.2% per year between the years of 1997 and 2007. Additionally, in some countries (e.g., Japan), NTM pulmonary infection incidence rates from 2007 to 2014 surpassed that of tuberculosis. In the US, the mortality rate of NTM pulmonary disease, often caused by *Mycobacterium avium* complex, *Mycobacterium kansasii*, or *Mabs*, increased between 1999 and 2014 with older white women experiencing the greatest mortality burden. Although NTM infections can occur in apparently healthy individuals, infection primarily develops in vulnerable hosts, such as immunocompromised individuals, the elderly, and patients with pre-existing inflammatory lung diseases (e.g., cystic fibrosis).

*Mabs* infections is one of the most clinically challenging NTM infections and is classified as three subspecies: *Mabs* subsp. *abscessus, Mabs* subsp. *massiliense*, and *Mabs* subsp. *bolletii*. *Mabs* is the third most frequently recovered respiratory NTM in the US, particularly among individuals with compromised lung defenses, and accounts for 65-80% of rapidly growing NTM isolates. *Mabs* pulmonary infections are most severe in patients with cystic fibrosis (CF) or chronic obstructive pulmonary disease, which leads to a decline in lung function resulting in a mortality rate of 69%. *Mabs* and *M. avium* are considered major causes of bronchopulmonary infections in CF patients, with 3-10% and 60-80% of patients in the US and Europe being affected with *Mabs* and *M. avium*, respectively.

The major threat posed by *Mabs* is its resistance to classical anti-tuberculosis drugs, such as isoniazid and rifampin, and current antibiotics, leading to a lack of effective drug regimens. The American Thoracic Society recommends macrolides (clarithromycin and azithromycin), in combination with intravenous amikacin and cefoxitin (or imipenem) for at least one year until sputum samples are culture negative. Although macrolide-based therapy is the typical treatment, *Mabs* infections may respond poorly to macrolides due to the presence of inducible macrolide resistance genes, such as the erm gene, or mutations within the drug binding-pocket of the 23S rRNA gene. While *Mabs* subsp. *massiliense* has a nonfunctional erm gene and is susceptible to macrolides, *Mabs* subsp. *abscessus* and *Mabs* subsp. *bolletii* confer macrolide resistance. Since *Mabs* subspecies are difficult to distinguish by hospital laboratories, current research has focused on the identification and differentiation of subspecies during an infection in order to allow for more effective management of pulmonary disease. *Mabs* pulmonary infections have no known effective drug treatments. Currently, the only cure for *Mabs* pulmonary disease is surgical lung resection and concurrent multidrug therapy. Although antibiotic administration can improve *Mabs* symptoms, these same antibiotic regimens are often associated with adverse side effects. Furthermore, even after multidrug therapy, *Mabs* infections have an estimated 50% recurrence rate.

Two distinct morphotypes of *Mabs* are displayed when plated on solid agar media: a smooth (S), biofilm forming, non-cording variant, and a rough (R), non-biofilm forming, cording variant. The major difference between the two morphotypes is the presence of cell wall glycopeptidolipids (GPL) in the S variant, while the R variant is deficient in GPL. Clinically, the S variant colonizes the lung in a susceptible host, while the R variant appears after colonization has occurred. While both S and R morphotypes can grow in macrophages, the R variant is more virulent and more resistant to macrophage killing and is associated with more severe and persistent pulmonary infections. While transition from an S to R morphotype occurs spontaneously during host infection, clinical respiratory specimens have similar occurrences with 50% R and 38% S. R morphotype clinical isolates can become more attenuated upon spontaneous reversion to an S morphotype.

Due to its acquired and intrinsic antibiotic resistance to classical anti-tuberculous drugs, most antibiotics, and disinfectants novel approaches to treating *Mabs* infections and eradicating the disease are needed. For the treatment of NTM pulmonary infections, AMPs are more potent and have fewer side effects than orally and intravenously administered antibiotics and can be delivered as an inhaled therapeutic. In addition, inhaled AMPs, similar to inhaled antibiotics, fail to cross the respiratory epithelium, and therefore, reduce off-target effects and increase lung bioavailability. Currently no naturally occurring peptides nor their derivatives are recommended to treat *Mabs* infections.

For the treatment of NTM pulmonary infections, AMPs can be more potent and have fewer side effects than orally and intravenously administered antibiotics and can be delivered as an inhaled therapeutic. Although inhaled antibiotics achieve far higher concentrations with fewer side effects than orally delivered antibiotics to treat respiratory disease, inhaled AMPs are, in general, unable to cross the respiratory epithelium, therefore, reducing off-target effects and increasing lung bioavailability.

As shown in the examples, *Mabs* was screened against 125,000 synthetic peptides, containing both D- and L-amino acids, on a high-density peptide microarray, identifying 27 interacting peptides which were 17 amino acids long with 4-6 positively charged amino acids. MIC assays in M7H9, MHB, and CAMHB culture media identified six peptides that significantly inhibited *Mabs*. These peptides were hydrophobic (24-47%), non-acidic, and were rich in Arg, Val, Asn, and Phe (Table 1). The peptides (ASU2001, ASU2009, ASU2019, ASU2056, ASU2059, ASU2060) were further screened against both *Mabs* smooth and rough morphotypes to determine the impact of cell wall GPLs on activity. All six peptides displayed increased activity against the *Mabs* smooth morphotype, suggesting that interactions with cell wall GPLs are important for antibacterial activity. Additionally, all peptides exhibited increased inhibition in the presence of EDTA, suggesting that sequestering divalent metal cations enhances peptide interactions with *Mabs*.

TABLE 1

Peptides with Mabs inhibitory activity.

| Peptide Name | Peptide Sequence[a] | Molecular Weight (Daltons) | Number of Positively Charged Residues | Hydrophobicity (%) |
|---|---|---|---|---|
| ASU2001 | QFNGrSkaAkVNFw rka (SEQ ID NO. 1) | 2007.37 | 5 | 41 |
| ASU2009 | rYGlSkArkVNQFr kal (SEQ ID NO. 2) | 2034.51 | 6 | 35 |
| ASU2019 | rVGPSAPHNlFrrk Sal (SEQ ID NO. 3) | 1905.29 | 5 | 47 |
| ASU2056 | QrwGlSlAPYkNFr rlS (SEQ ID NO. 4) | 2091.50 | 4 | 41 |
| ASU2059 | YGrSArYNrrklGa lSG (SEQ ID NO. 5) | 1924.27 | 5 | 24 |
| ASU2060 | VGrwSArYNFrwrk SGl (SEQ ID NO. 6) | 2138.51 | 5 | 35 |

[a]Lower-case letters signify D-amino acids

EXAMPLES

The present invention is further illustrated by the following examples that should not be construed as limiting. The contents of all references, patents, and published patent applications cited throughout this application, as well as the Figures, are incorporated herein by reference in their entirety for all purposes.

Example 1

Materials and Methods i. *Mabs* Strains and Growth Conditions.

*Mabs* ATCC 19977 smooth morphotype (*Mabs* 19977S) cells were cultured at 37° C. in Middlebrook 7H9 supplemented with albumin, dextrose, and catalase (ADC) (10%), Tween 80 (0.05%), and glycerol (0.2%) (herein referred to as M7H9). *Mabs* 19977S was exposed to clarithromycin (8 µg/ml) in M7H9 for 24 h at 37° C., subjected to serial dilutions and plated on Middlebrook 7H10 agar supplemented with oleic acid, albumin, dextrose, and catalase (OADC) (herein referred to as M7H10). After 5 d incubation at 37° C., a single, isolated colony displaying a rough morphotype (*Mabs* 19977R) was detected, grown, and stored at −70° C. *Mabs* 19977S and *Mabs* 19977R were grown for approximately 32 h at 37° C., diluted 1:100 in fresh, pre-warmed M7H9, and grown for an additional 14 h until the cultures reached early-to-mid-logarithmic phase (OD600=0.2-0.3).

ii. *P. aeruginosa*, *E. coli*, *K. pneumoniae*, and Methicillin Resistant *S. aureus* Strains and Growth Conditions.

*P. aeruginosa* (ATCC 27853) and methicillin-resistant *S. aureus* (MRSA) USA300 were cultured at 37° C. in Tryptic Soy Broth (TSB). *E. coli* (ATCC 25922) and *K. pneumoniae* (ATCC 13883) cells were cultured in Luria broth (LB). After 16 h incubation, *P. aeruginosa*, *E. coli*, and *K. pneumoniae* cultures were centrifuged (3,715×g) for 3 min, resuspended in sterile 0.9% saline, and adjusted to $OD_{600}$ of 0.4, 0.07, and 0.1 for *P. aeruginosa*, *E. coli*, and *K. pneumoniae*, respectively. MRSA was cultured at 37° C. in TSB for 18 h before centrifugation at 3,715×g for 3 min. MRSA was then resuspended in MHB and diluted to $OD_{600}$ of 0.1 (approximately $10^7$ CFU/ml) in sterile 0.9% saline. Bacterial preparations were serially diluted in MHB to approximately $10^5$ CFU/ml for use in the assays.

iii. *E. coli* Clinical Isolates.

De-identified excess and residual clinical urine samples were obtained from the clinical microbiology laboratory at Mayo Clinic Hospital, Phoenix, Ariz. (approved by Mayo Clinic Biospecimen Subcommittee BIO00015462). *E. coli* urinary tract infection clinical isolates were cultured as described above and stored at −70° C.

iv. Peptide Microarrays.

The high-density (HD) peptide microarrays were synthesized in house with a library of peptides on a silicon wafer coated with a photoresist and a photoacid generator, according to our published methods (Legutki et al., "Scalable high-density peptide arrays for comprehensive health monitoring." *Nat Commun.* 2014, 5). Micron scale regions of photoacid are generated and exposed to protected amino acids. If acid is present, the amino acid is de-protected and coupled. Through subsequent steps, peptides are synthesized, forming a microarray of 123,816 peptides with unique sequence compositions. Replicate peptide microarrays are produced in a standard microscope slide sized format with a geometry that is compatible with a standard 96-well microtiter plate, thereby enabling standard robotics and plate washers to be used for the binding assays. Prior to screening, slides were placed in a four-slide chamber (ArrayIt, Sunnyvale, Calif.) and blocked for 1 h in 150 µL of 3% BSA in PBS, pH 7.4 with 0.05% Tween 20 (PBST) and agitation (300 rpm). Slides were washed three times in PBST using a plate washer (Beckman Coulter Biomek, Indianapolis, Ind.).

v. *Mabs* Screening on Peptide Microarrays.

*Mabs* cultures were prepared as described above, centrifuged, and washed three times in PBST. Two biological replicates of *Mabs* 19977S or *Mabs* 19977R cells (~1.0×10$^8$ CFU/ml) were labeled with 200 µg of AF647-NHS (ThermoFisher Scientific, Carlsbad, Calif.) in pre-warmed PBST. Two biological replicates of *Mabs* 19977S or *Mabs* 19977R cells (~3×10$^8$ CFU/ml) were labeled with 50 µg of Cell Tracker Orange (CTO) CMRA (ThermoFisher Scientific) in pre-warmed PBST. Cells were incubated with AF647 or CTO for 1 h at room temperature or 37° C., respectively, with shaking at 250 rpm. Fluorescently labeled bacterial cells were washed, resuspended in 3% BSA in PBST to achieve a concentration of ~10$^8$ CFU/mL, and diluted to 1×10$^7$ CFU/mL in a 96-well microtiter plate. The cells were transferred to the slide chamber at 150 µL per well and incubated on a shaker (ThermoMixer, Eppendorf, Hauppauge, N.Y.) for 1 h at 37° C. at 300 rpm. The slide was washed three times in PBST, three times in water, dried, and scanned on an Innoscan 900AL microarray scanner (Innopsys, Carbonne, France). Data were analyzed using GenePix, and raw data files were analyzed using Microsoft Excel and JMP statistical software (Cary, N.C.).

vi. Identification of Peptides with Activity Against *Mabs*.

Bacteria grown in M7H9, MHB, and cation-adjusted MHB (CAMHB) were used to identify unpurified peptides with inhibitory activity against *Mabs* 19977S and *Mabs* 19977R. Peptides (50-65% purity) were synthesized by Sigma Aldrich (St. Louis, Mo.) PEPscreen Custom Peptide Libraries. *Mabs* ATCC 19977S and ATCC 19977R mid-logarithmic phase cultures were centrifuged (3,715×g) for 2 min, washed in pre-warmed M7H9, re-suspended in M7H9, MHB, or CAMHB, and diluted to 10$^6$ CFU/ml. In a 96-well polystyrene microtiter plate, media (M7H9, MHB, or CAMHB), unpurified peptides (100 µM or 10 µM), ethylenediaminetetraacetic acid (EDTA) (100 µM), and cells (*Mabs* 19977S or *Mabs* 19977R) (10$^5$ CFU/ml) were added. EDTA was added to determine if metal ion chelation would alter peptide activity. Clarithromycin (4 µg/ml) was used as an antibiotic positive control. The 96-well microtiter plates were statically incubated at 37° C. for 72 h. The OD$_{600}$ was measured every 24 h using a SpectraMax M2 microplate reader (Molecular Devices, San Jose, Calif., USA). Peptides that reduced *Mabs* growth by ≥50%, when compared to the growth control OD$_{600}$, were considered active.

vii. *Mabs* Microdilution Antimicrobial Assays with Purified Peptides.

Peptides with activity against *Mabs* were synthesized and purified (90-100% purity) by WatsonBio Sciences (Houston, Tex., USA). In order to determine effects on *Mabs* viability, microdilution antimicrobial assays were performed in MHB. *Mabs* 19977S and *Mabs* 19977R mid-logarithmic phase cultures were prepared and processed as described above. In a 96-well microtiter plate, MHB, two-fold serial dilutions (256-2 µM) of purified peptides, EDTA (100 and cells (*Mabs* 19977S or *Mabs* 19977R) (10$^5$ CFU/ml) were added. Clarithromycin (4 µg/ml) was used as an antibiotic positive control. Microtiter plates were statically incubated at 37° C. for 96 h. The OD$_{600}$ was measured every 24 h using a SpectraMax M2 microplate reader (Molecular Devices, San Jose, Calif., USA).

viii. Identification of Peptides with Cross-Inhibitory Activity Against *P. aeruginosa*, *E. coli*, and *S. aureus*.

*P. aeruginosa*, *E. coli*, and MRSA stationary phase cultures were diluted to 10$^6$ CFU/ml. In a 96-well polystyrene microtiter plate, MHB, purified peptides [at their respective minimum inhibitory concentration (MIC) values against *Mabs*], EDTA (100 and cells (*P. aeruginosa*, *E. coli*, *K. pneumoniae*, or MRSA) (10$^5$ CFU/ml) were added. Amikacin (6 and 3 µg/ml), vancomycin (8 and 4 µg/ml), and ampicillin (32 and 16 µg/ml) were used as antibiotic controls. The 96-well microtiter plates were statically incubated at 37° C. for 24 h after which samples from each well were subjected to serial dilutions in sterile 0.9% saline and plated on MHA in duplicate. Colonies were counted to determine CFU/ml viability.

ix. Determination of ASU2060 MIC Against *E. coli* Clinical Isolates.

The MICs of ciprofloxacin, cefazolin, ampicillin, and nitrofurantoin against the *E. coli* clinical isolates were determined in triplicate to establish antibiotic susceptibility profiles for each isolate (n=6). To determine the MIC of antibiotics and ASU2060, isolates were cultured in LB for 16 h, centrifuged (3,715×g) for 1 min, resuspended in MHB, and diluted to ~10$^7$ CFU/ml (OD$_{600}$=0.05). Samples were serially diluted in MHB to ~10$^5$ CFU/ml and added to a 96-well polystyrene plate prepared with ASU2060 (128-4 µM). After incubation for 22 h at 37° C., the OD$_{600}$ was measured using a SpectraMax M2 microplate reader (Molecular Devices, San Jose, Calif., USA). Values were normalized to the medium blank (MHB) and *E. coli* (ATCC 25922) treated with nitrofurantoin at 64 µM.

x. Cytotoxicity Assessment of *Mabs* Inhibitory Peptides.

To determine if the purified, *Mabs* inhibitory peptides were toxic, human red blood cell (hRBC) hemolytic assays were performed. Peptides (at 1×, 2×, and 4× their respective *Mabs* 19977S MICs) were added to 4% hRBC in saline and statically incubated for 1 h or 18 h at 37° C. Triton X-100 (1%) was used as a positive control and resulted in complete hRBC lysis. Following incubation, the peptide-hRBC mixtures and the 1% Triton X-100 positive controls were centrifuged for 1 min at 1,000×g to pellet the intact hRBC. The supernatant for each experimental mixture and control was removed, and OD$_{475}$ measurements were recorded to determine the percentage of lysed hRBC. The percentage of hemolytic activity was normalized by comparing the supernatant absorbance of all conditions tested to an equivalent number of hRBC lysed with 1% Triton X-100 (Eq. 1) (50).

$$\text{Percent cytotoxicity} = \frac{OD_{475} \text{ experimental mixture supernatant}}{OD_{475} \text{ positive control supernatant}} \times 100\% \quad \text{Eq. 1}$$

xi. Serum Stability Assays.

The collection and use of all human serum for research presented here was approved by the Institutional Review Board of Arizona State University, protocol No. 0912004625. Informed consent was obtained from all human subjects. Blood was collected from five healthy donors and the serum was separated. Serum samples were pooled and stored at −70° C. prior to experimental use. ASU2060 was incubated with 20% pooled, human serum for various intervals (1-24 h). At each time point, sample aliquots were removed and mixed with cOmplete, EDTA-free protease inhibitor (11873580001, Roche, Indianapolis, Ind.). ASU2060 serum stability was determined by examining retained biological activity in a 24-hour bactericidal assay with *E. coli* ATCC 25922 (~2×10$^5$).

xii. Statistical Analyses.

All analyses were performed with GraphPad Prism software Version 9.0.2. Statistical significance was determined using two-way ANOVA and t-tests with P<0.05.

Example 2

*Mabs* ATCC 19977 Variants

Despite similar S and R morphotype susceptibility to clarithromycin, amikacin, and cefoxitin, there are differences in virulence and host-pathogen interactions. Active peptides against both *Mabs* S and R variants were screened. After exposure of *Mabs* 19977S to clarithromycin, a subpopulation of cells frequently exhibited a rough morphology phenotype on M7H10 agar without antibiotics (FIG. 1A). The rough variant, *Mabs* 19977R, did not revert to a smooth morphotype and was stably maintained during in vitro growth, thereby allowing peptide microarray screening of both *Mabs* 19977S and *Mabs* 19977R cells.

Example 3

High Throughput Screening: *Mabs* Morphotype Binding on HD Peptide Microarrays

Figure 1B:
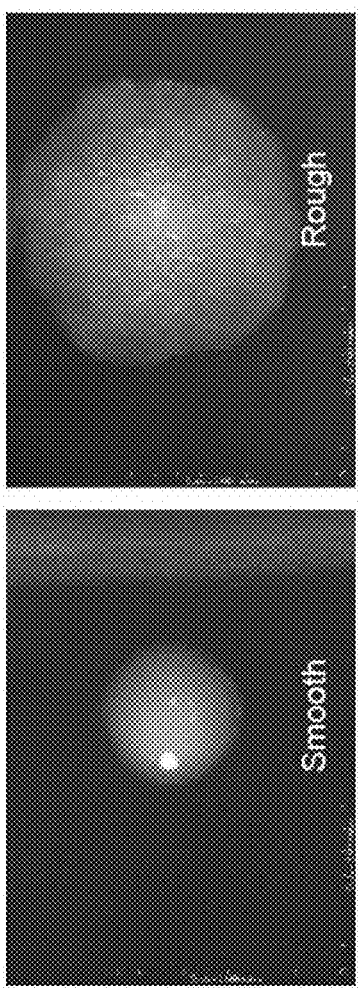
FIG. 1B depicts, in accordance with certain embodiments, CTO labeled (left) or AF647 labeled (right) Mabs binding to a peptide spot on the peptide microarray.
Figure 1D:
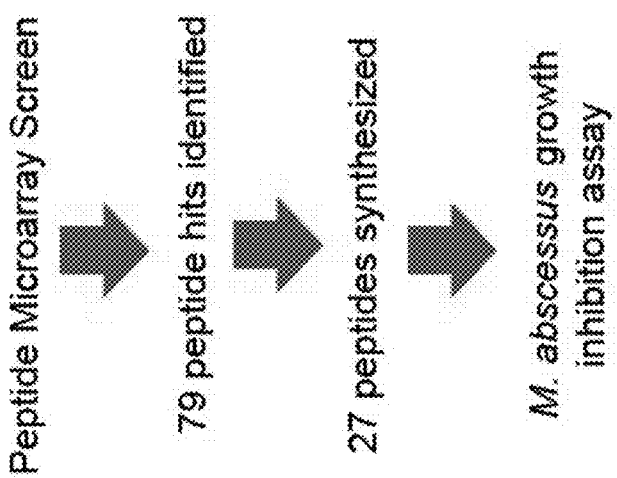
FIG. 1D illustrates, in accordance with certain embodiments, a workflow to select and test synthetic peptides with antimicrobial properties against Mabs.
Figure 1C:
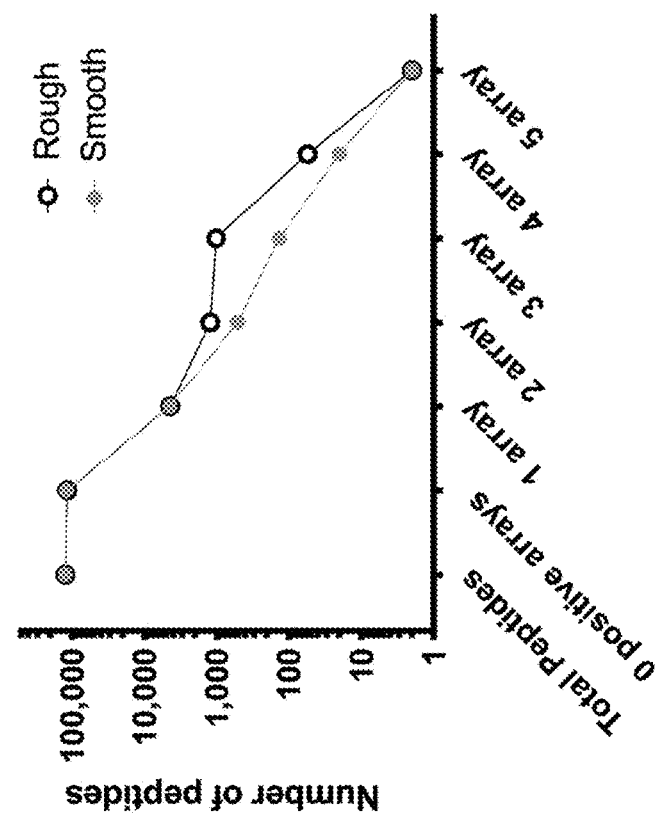
FIG. 1C illustrates, in accordance with certain embodiments, statistics of bacteria binding signals to the peptide microarrays.

*Mabs* 19977S or *Mabs* 19977R cells were labeled with either amine-reactive Alexa Fluor 647 (AF647), which binds and fluoresces the cell surface, or Cell Tracker Orange (CTO), which fluoresces after internalization into the cytoplasm, and incubated on replicate peptide microarrays (n=12). One notable adaptation from spotted peptide microarrays to the in situ synthesized HD peptide microarrays is the reduction in spot size. The HD microarrays have smaller features (14 µm×14 µm squares) than spotted peptide microarrays (~80 µm diameter circles), reducing the number of bacteria that can bind a given spot (FIG. 1B). In previous studies, bacteria bound to a given peptide spot revealed several thousand relative fluorescence units (RFU), while signals were close to background for non-binding peptides. *Mabs* bound far fewer peptides than *S. aureus* or *P. aeruginosa* when incubated on a similar HD peptide microarray. While there are typically few bacteria bound to a single peptide feature, the use of 12 replicate arrays per condition enables a counting approach to be used for peptide identification. Essentially, by counting the number of times a peptide bound *Mabs* across the 12 replicate arrays, a relative measure of peptide for each *Mabs* morphotype was obtained (FIG. 1C). By defining bacterial binding as RFU>10 times the array median signal for AF647 or CTO and counting the number of times a given peptide was positive for the 12 morphotype replicates, a small number of peptides (n=79) were positive in four or more arrays per morphotype. From these peptides, 27 peptides were selected for synthesis and subsequent testing based upon array reactivity and peptide properties (FIG. 1D).

Example 4

Identification of Unpurified Peptides with Activity Against *Mabs* During Growth in M7H9, MHB, and CAMHB To evaluate if the 27 unpurified peptides had in vitro activity, *Mabs* 19977S and *Mabs* 19977R were incubated with the peptides at 100 µM and 10 with or without EDTA (100 in M7H9 broth, MHB, and CAMHB for 96 h. In M7H9 broth, five peptides (ASU2001, ASU2009, ASU2019, ASU2056, and ASU2059; 100 µM) exhibited activity against both morphotypes when EDTA was added (FIGS. 2A and 2B). Additionally, four peptides (ASU2060, ASU2061, ASU2062, and ASU2070; 100 µM) were active against the *Mabs* 19977S smooth morphotype only, when EDTA was added (FIG. 2B). When EDTA was not added, the smooth-acting peptides (ASU2060, ASU2061, ASU2062, and ASU2070; 100 µM) displayed less activity (FIG. 2A). One peptide (ASU2001; 100 µM) exhibited activity against the *Mabs* 19977R rough morphotype in the presence or absence of EDTA (FIGS. 2A and 2B). In MHB, fourteen peptides (100 µM) exhibited activity against both morphotypes when EDTA was added (FIG. 2D). Five of the fourteen peptides (ASU2001, ASU2009, ASU2019, ASU2056, and ASU2059) that had activity against both morphotypes in M7H9 maintained activity in MEM when EDTA was added (FIG. 2D). Three of the four smooth-acting peptides (ASU2061, ASU2062, and ASU2070) (100 µM) that had activity in M7H9 with EDTA maintained inhibitory activity in MHB when EDTA was added (FIG. 2D). Without EDTA supplementation, none of the peptides displayed activity against *Mabs* in MEM (FIG. 2C). In culture medium with cation supplementation (CAMHB), ASU2060 (100 µM) had activity against both morphotypes when EDTA was added (FIG. 2F). ASU2060 also exhibited smooth-specific activity in M7H9 when EDTA was added (FIG. 2B). There were no peptides with inhibitory activity in CAMHB without EDTA (FIG. 2E). At lower concentrations of 10 µM, peptides lacked activity against *Mabs* 19977S and *Mabs* 19977R morphotypes in M7H9 broth, MEM, or CAMHB regardless of the addition of EDTA (FIG. 3).

Example 5

*Mabs* Microdilution Inhibitory Assays with Purified Peptides

Figure 4A:
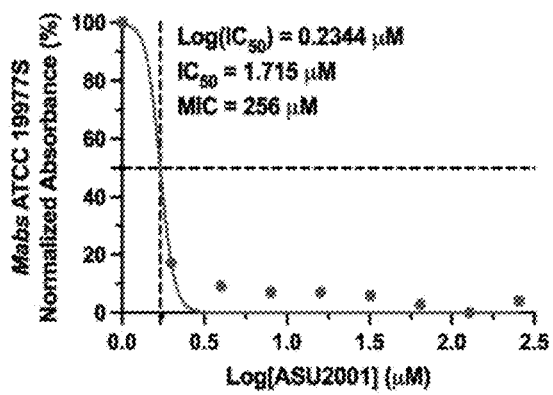
FIGS. 4A-4F depict, in accordance with certain embodiments, the $IC_{50}$ and MIC values of synthetic peptides ASU2001 (FIG. 4A), ASU2009 (FIG. 4B), ASU2019 (FIG. 4C), ASU2056 (FIG. 4D), ASU2059 (FIG. 4E), and ASU2060 (FIG. 4F) against Mabs ATCC 19977S smooth morphotype in MHB supplemented with EDTA (100 µM) with 96 h incubation at 37° C. Three independent experiments were performed with the average of all three replicates plotted for each peptide. Absorbance ($OD_{600}$) values were normalized to the growth control (100%), and $IC_{50}$ values were determined by nonlinear regression.
Figure 4B:
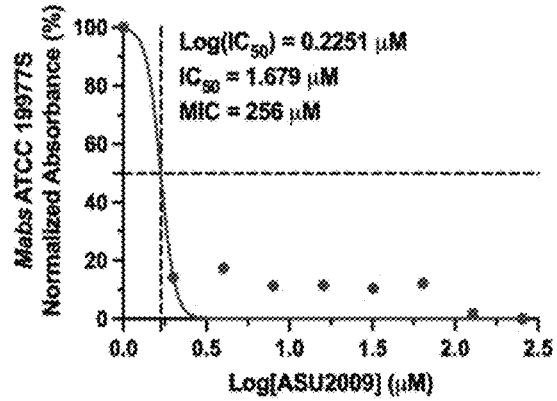
Figure 4C:
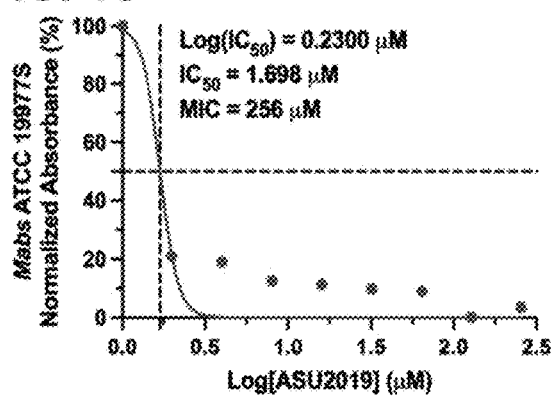
Figure 4D:
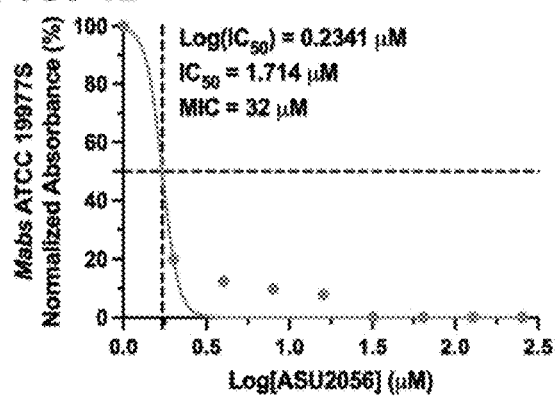
Figure 4E:
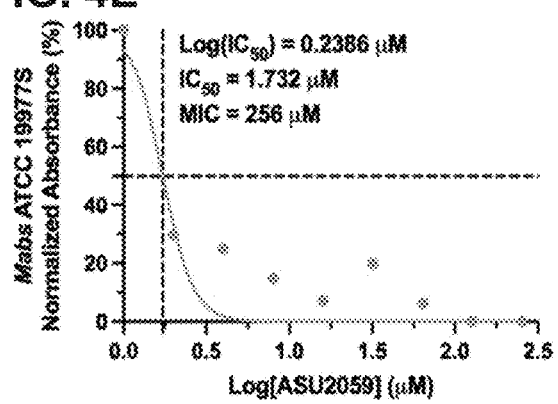
Figure 4F:
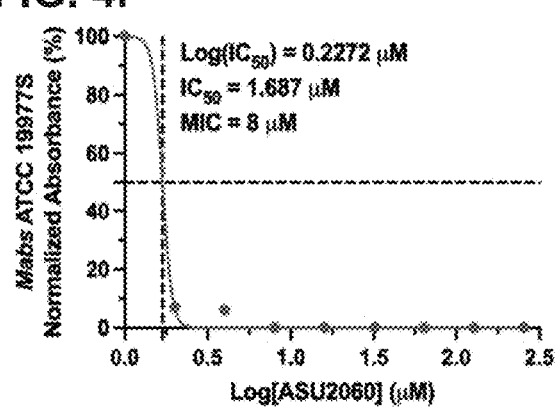
Figure 5A:
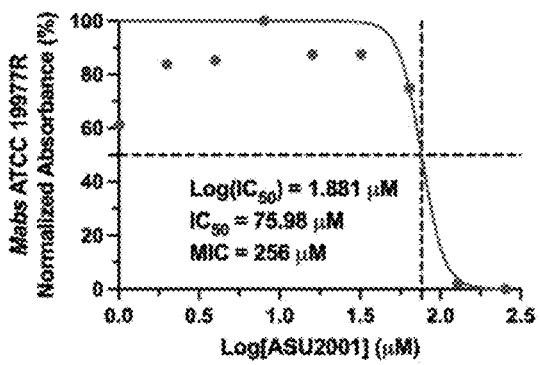
FIGS. 5A-5F depict, in accordance with certain embodiments, the $IC_{50}$ and MIC values of synthetic peptides ASU2001 (FIG. 5A), ASU2009 (FIG. 5B), ASU2019 (FIG. 5C), ASU2056 (FIG. 5D), ASU2059 (FIG. 5E), and ASU2060 (FIG. 5F) against Mabs ATCC 19977S rough morphotype in MHB supplemented with EDTA (100 µM) with 96 h incubation at 37° C. Three independent experiments were performed with the average of all three replicates plotted for each peptide. Absorbance ($OD_{600}$) values were normalized to the growth control (100%), and $IC_{50}$ values were determined by nonlinear regression.
Figure 5B:
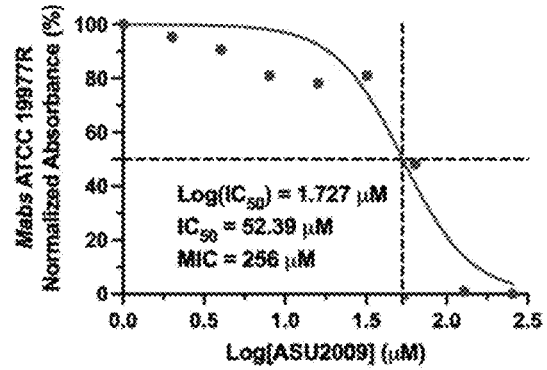
Figure 5C:
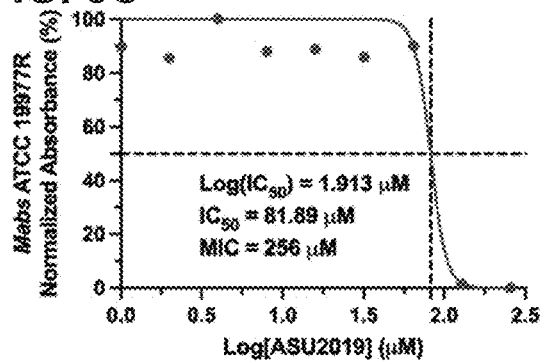
Figure 5D:
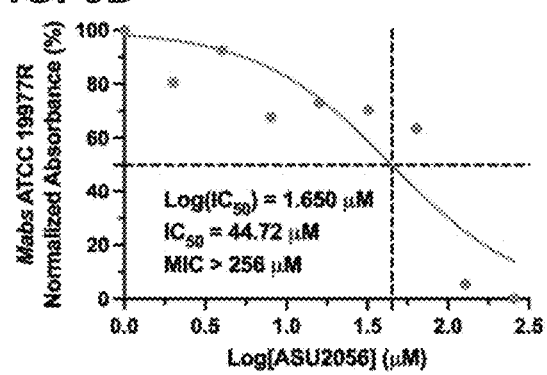
Figure 5E:
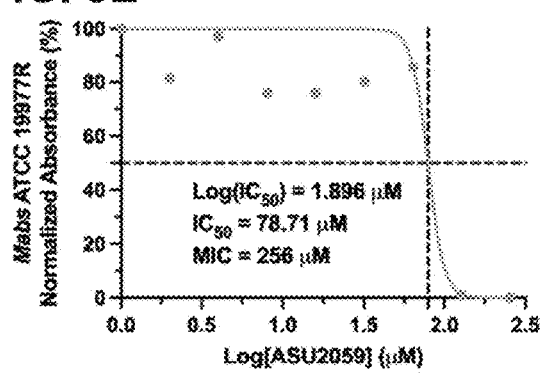
Figure 5F:
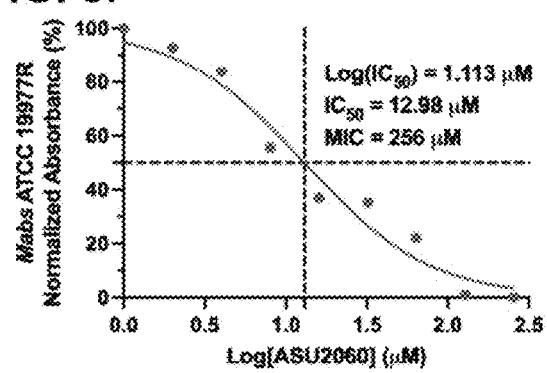

Peptides with activity against *Mabs* (ASU2001, ASU2009, ASU2019, ASU2056, ASU2059, and ASU2060) were synthesized and purified (90-100% purity) by WatsonBio Sciences (Houston, Tex., USA). To determine the effects of *Mabs* inhibition, microdilution inhibitory assays were performed with the peptides two-fold serially diluted from 256 μM in MHB, with EDTA (100 μM), for 96 h. From these assays, ASU2001, ASU2009, ASU2019, and ASU2059 had $IC_{50}$ values<1.8 μM and MIC values of 256 μM against *Mabs* 19977S (FIGS. 4A-4C and 4E). ASU2056 and ASU2060 peptides displayed the greatest potency against *Mabs* 19977S with MIC values of 32 and 8 respectively (FIGS. 4D and 4F). Against *Mabs* 19977R, the six peptides displayed calculated $IC_{50}$ values that were 8-46 times higher than against *Mabs* 19977S (FIGS. 4A-5F). ASU2001, ASU2019, and ASU2059 peptides revealed half maximal inhibitory concentrations of 76-82 μM against *Mabs* 19977R (FIGS. 5A, 5C, and 5E), while ASU2009 and ASU2056 $IC_{50}$ values were lower at 52 and 45 μM, respectively (FIGS. 5B and 5D). Similar to *Mabs* 19977S, ASU2060 displayed greatest potency against *Mabs* 19977R with an $IC_{50}$ value of 13 μM (FIG. 5F). Based on the results from the high-throughput HD peptide arrays of 123,816 randomly-synthesized peptides and all *Mabs* microdilution inhibitory assays, two promising hit peptides, ASU2056 and ASU2060, were selected for additional experiments. Notably, not all potential antimicrobial peptide hits were pursued.

Example 6

Figure 6A:
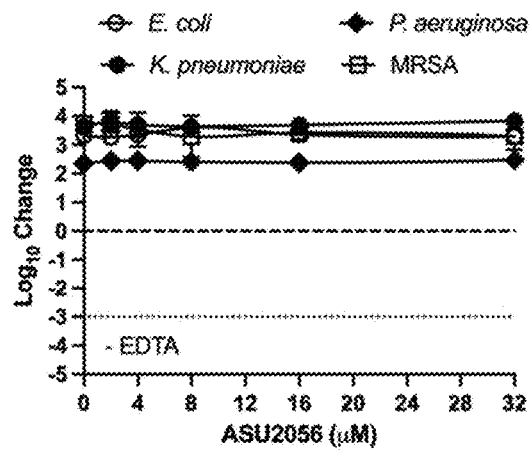
FIGS. 6A-6D depicts, in accordance with certain embodiments, the antimicrobial activity of synthetic peptides ASU2056 (FIGS. 6A and 6B) and ASU2060 (FIGS. 6C and 6D) against *Escherichia coli, Klebsiella pneumoniae, Pseudomonas aeruginosa*, methicillin-resistant *Staphylococcus aureus* (MRSA). The peptides were incubated with each bacterium in MHB at MICs determined against *Mabs* 19977S with 100 µM EDTA (FIGS. 6B and 6D) and without EDTA (FIGS. 6A and 6C). Three independent experiments were performed with the average of all three replicates plotted and error bars representing the standard error of the mean (SEM). $Log_{10}$ change was normalized to the initial concentration for each replicate. The dashed line indicates starting concentration, while the dotted line indicates the bactericidal threshold (99.9%).
Figure 6B:
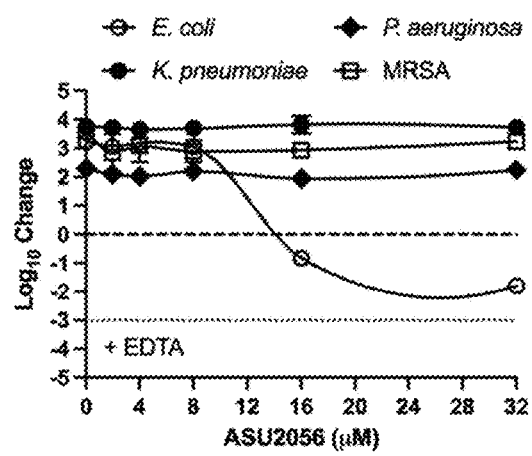
Figure 6C:
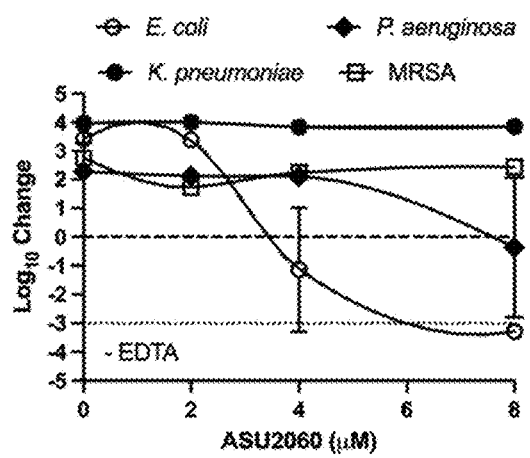
Figure 6D:
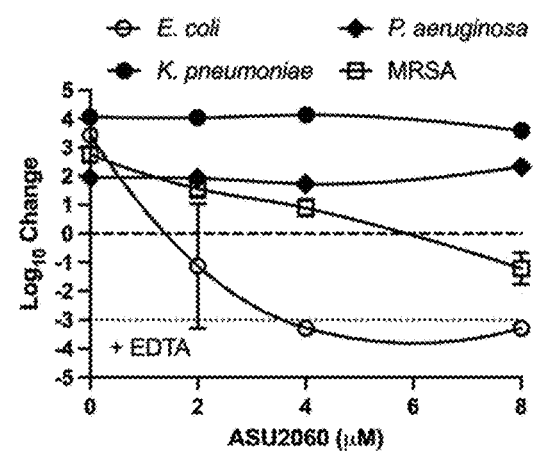

Peptide Inhibitory Activity Against *E. coli, P. aeruginosa, K. pneumoniae*, and MRSA USA300, During MHB Growth To determine if ASU2056 (32 μM; *Mabs* MIC) and ASU2060 (8 μM; *Mabs* MIC) have in vitro activity against other microorganisms of interest, *E. coli, P. aeruginosa, K. pneumoniae*, and MRSA USA300 cells were incubated with the peptides in MHB with and without EDTA (100 μM) for 24 h. Without EDTA supplementation, ASU2056 lacked activity against the four bacteria (FIG. 6A). In the presence of EDTA, ASU2056 inhibited *E. coli* at 16 and 32 μM concentrations, but did not alter *P. aeruginosa, K. pneumoniae*, or MRSA growth (FIG. 6B). ASU2060 displayed bactericidal activity against *E. coli* at concentrations of 8 μM and 4 μM in the absence and presence of EDTA, respectively (FIGS. 6C and 6D). ASU2060 (8 μM) without EDTA inhibited *P. aeruginosa* (FIG. 6C) but lacked *P. aeruginosa* activity in the presence of EDTA (FIG. 6D). Conversely, ASU2060 (8 μM) with EDTA inhibited MRSA (FIG. 6D) but lacked MRSA activity in the absence of EDTA (FIG. 6C). Neither ASU2056 or ASU2060 had activity against *K. pneumoniae* (FIGS. 6A-6D). Collectively, the two promising anti-*Mabs* hit peptides, ASU2056 and ASU2060, also inhibit or kill *E. coli, P. aeruginosa*, or MRSA.

Example 7

Figure 7:
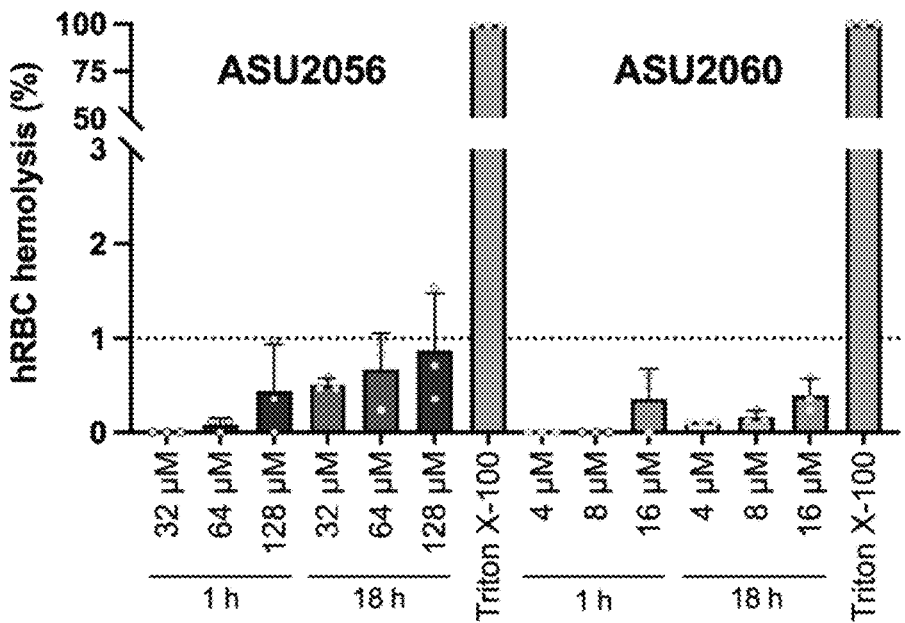
FIG. 7 illustrates, in accordance with certain embodiments, synthetic peptides ASU2056 and ASU2060 peptides lack of hRBC cytotoxicity. Human RBC hemolytic assays were performed with the ASU2056 and ASU2060 peptides at 1×, 2×, and 4×*Mabs* MIC concentrations with incubations of 1 and 18 h. All experiments, including Triton X-100 controls, were performed in triplicate with the bars representing the experimental mean, light grey dots representing individual biological replicates, and error bars representing the SD. The dotted line indicates 1% hRBC hemolysis.

ASU2056 and ASU2060 Purified Peptides Lack Human Red Blood Cell (hRBC) Hemolytic Activity To determine if the ASU2056 and ASU2060 exhibit eukaryotic cell toxicity, the two peptides were evaluated via hRBC hemolytic assays. The peptides were incubated with 4% hRBC for 1 h and 18 h at 1×, 2×, and 4× of their *Mabs* 19977S MIC values. When the ASU2056 and ASU2060 peptides were incubated for 18 h at 4×MIC concentrations of 128 and 16 μM, respectively, hRBC hemolysis averaged less than 1% (FIG. 7). Thus, neither ASU2056 nor ASU2060 exhibited significant human red blood cell hemolytic activity even after 18-hour incubation. ASU2060 was tested for serum stability and retained antibacterial activity after pre-incubation in human serum for 24 h.

This level of serum stability, potent activity, along with low initial toxicity assessment suggests that ASU2060 is a strong parent scaffold for further development and activity improvement. Importantly, the ASU2056 and ASU2060 peptides do not induce human erythrocyte hemolysis, suggesting that the peptides do not interact with or target eukaryotic cell membranes.

Example 8

Hemolytic Activity of Purified Peptides

Figure 8:
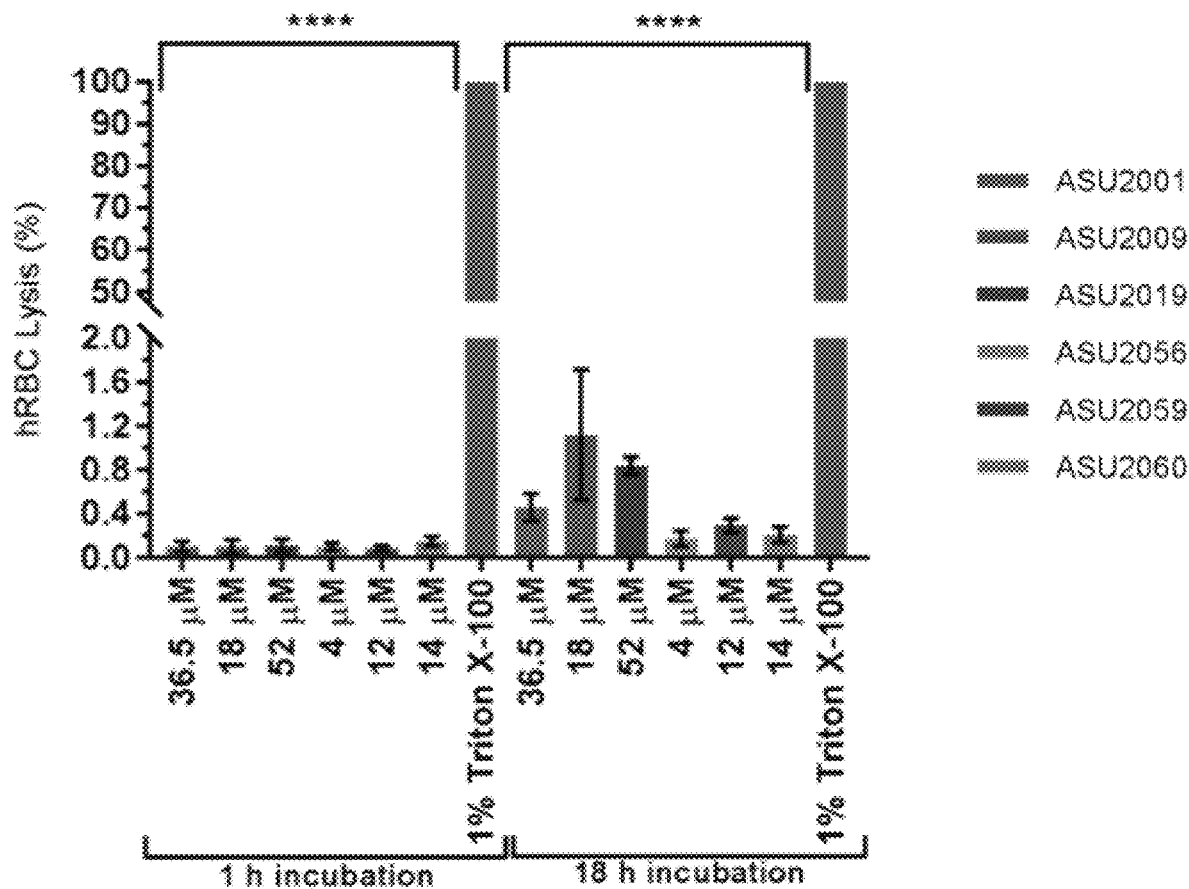
FIG. 8 illustrates results of toxicity experiments performed with the six *Mabs* inhibitory peptides (ASU2001, ASU2009, ASU2019, ASU2056, ASU2059, and ASU2060) through human red blood cell (hRBC) (4%) hemolytic assays. Peptides were incubated with hRBC for 1 h and 18 h at 37° C. Toxicity, signified through hemolytic activity, was measured hRBC supernatant OD475 measurements. The experimental and control data was compared to the 1% Triton X-100 control to determine significance. ****, adjusted p<0.001; one-way ANOVA with Dunnett's multiple comparisons test.
Figure 9:
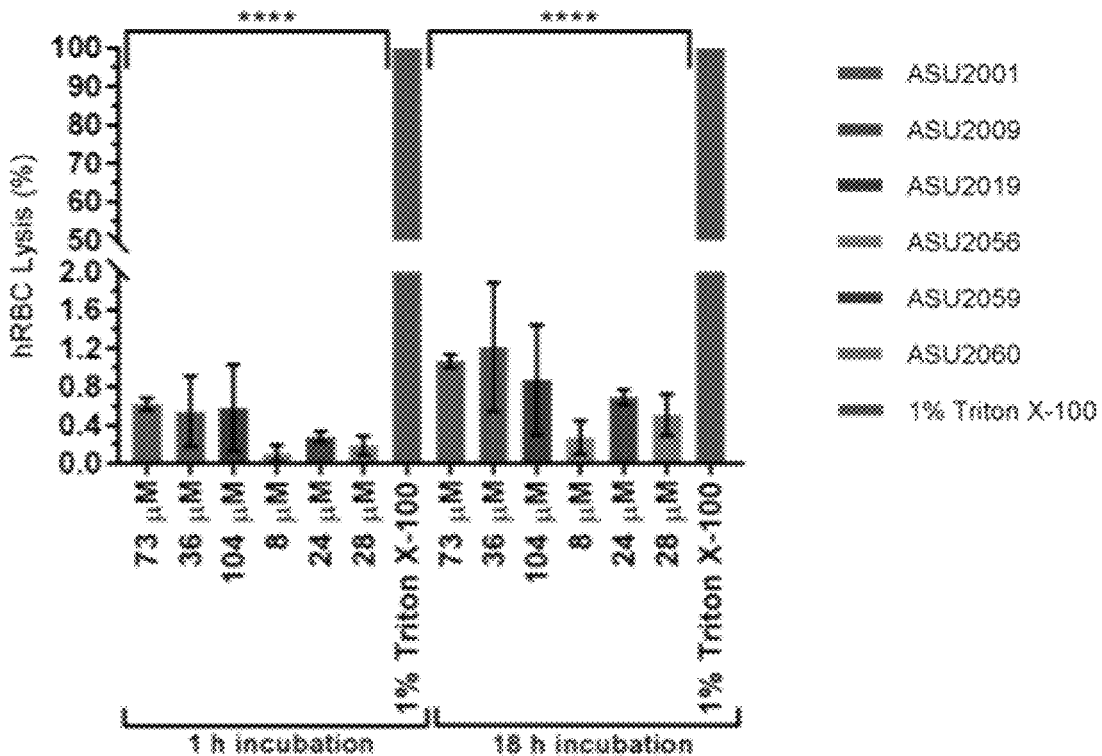
FIG. 9 illustrates results of toxicity experiments performed with the six *Mabs* inhibitory peptides (ASU2001, ASU2009, ASU2019, ASU2056, ASU2059, and ASU2060) through human red blood cell (hRBC) (4%) hemolytic assays. Peptides were incubated with hRBC for 1 h and 18 h at 37° C. Toxicity, signified through hemolytic activity, was measured hRBC supernatant OD475 measurements. The experimental and control data was compared to the 1% Triton X-100 control to determine significance. ****, adjusted p<0.001; one-way ANOVA with Dunnett's multiple comparisons test.
Figure 10:
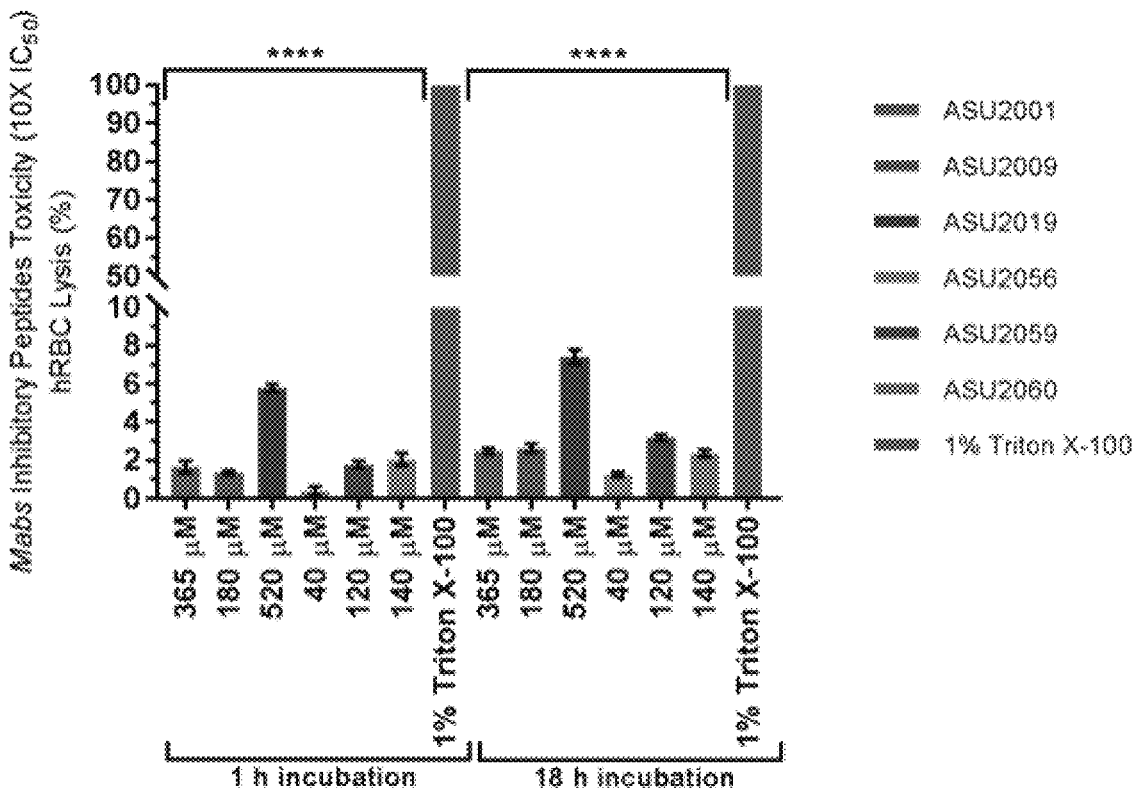
FIG. 10 illustrates results of toxicity experiments performed with the six *Mabs* inhibitory peptides (ASU2001, ASU2009, ASU2019, ASU2056, ASU2059, and ASU2060) through human red blood cell (hRBC) (4%) hemolytic assays. Peptides were incubated with hRBC for 1 h and 18 h at 37° C. Toxicity, signified through hemolytic activity, was measured hRBC supernatant OD475 measurements. The experimental and control data was compared to the 1% Triton X-100 control to determine significance. ****, adjusted p<0.001; one-way ANOVA with Dunnett's multiple comparisons test.

The toxicity of the purified peptides with activity against *Mabs* (ASU2001, ASU2009, ASU2019, ASU2056, ASU2059, ASU2060) was evaluated through hRBC (4%) hemolytic assays. The peptides were incubated with hRBC for 1 h and 18 h at 1×, 2×, and 10×, their respective *Mabs* IC50 concentrations. At 1× and 2×IC50 concentrations, all the peptides exhibited less than 2% hemolytic activity, when compared to the 1% Triton X-100 positive control (FIGS. 8 and 9). At 10×IC50 concentrations, all peptides had less than 10% hemolytic activity, when compared to the 1% Triton X-100 positive control (FIG. 10). While additional experiments are necessary to compare concentration-dependent toxicity, generally, ASU2019 had the most toxicity, while ASU2056 had the least toxicity. ASU2056, with its low hRBC toxicity and inhibitory activity against *Mabs* 19977S and *Mabs* 19977R, will likely serve as one of our lead peptides to advance for optimization and additional studies.

Example 9

Retained Antimicrobial Activity Indicates that ASU2060 is Stable in Human Serum

Figure 11:
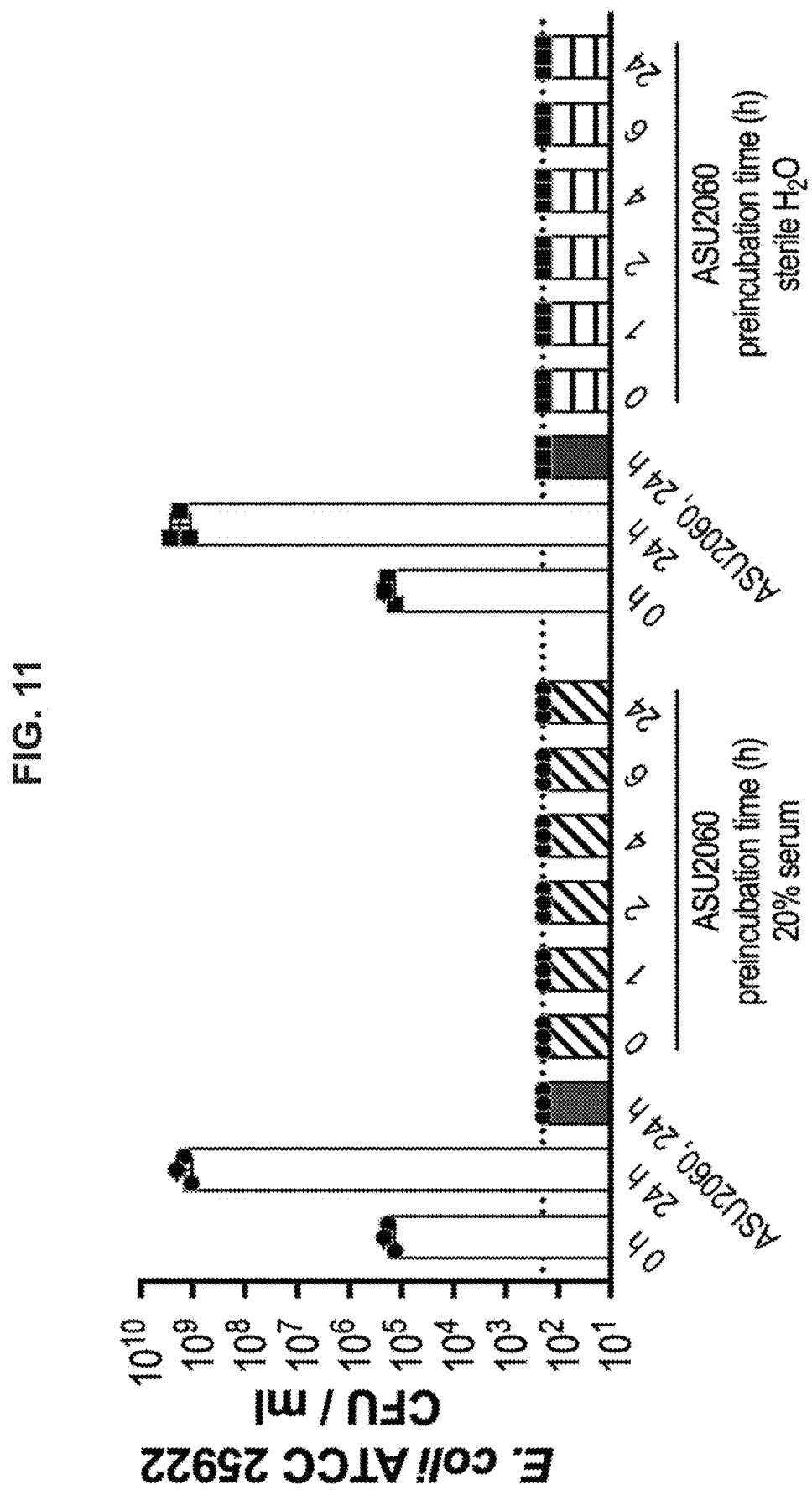
FIG. 11 illustrates, in accordance with certain embodiments, ASU2060 is stable in human serum and retains antibacterial activity when pre-incubated in human serum for 24 h. ASU2060 (16 µM; 2×MIC of *E. coli*) was pre-incubated in 20% pooled human serum (hatched bars) or sterile water (horizontal striped bars) at 37° C. prior to incubation with *E. coli* ATCC 25922 for 24 h. *E. coli* growth controls, 0 and 24 h, are shown as white bars. *E. coli* incubations with ASU2060 are shown as grey bars. Individual biological replicates for the 20% serum and sterile water experiments are represented as black circles and black squares, respectively. Data represent three independent experiments with SD.

To determine whether human serum-exposed ASU2060 retains biological stability, a 24-hour bactericidal assay with *E. coli* was performed. To assess the vulnerability of ASU2060 to human proteolytic degradation during therapeutic treatment, ASU2060 was exposed to 20% human serum for 1-24 h and subsequently analyzed ASU2060 bactericidal activity against *E. coli*. As shown in FIG. 11, ASU2060 (16 μM) retained *E. coli* bactericidal activity after preincubation with either 20% human serum or water for 24 h. This finding demonstrates ASU2060 stability and retention of antimicrobial activity in the presence of human proteases.

Example 10

ASU2060 Inhibits Antibiotic-Susceptible and Multidrug-Resistant *E. coli* Clinical Isolates The efficacy of ASU2060 against six *E. coli* clinical isolates with different antibiotic resistance profiles were (Table 2). The ASU2060 MIC against *E. coli* ATCC 25922 was determined to be 4 μM which was consistent with previous results. *E. coli* clinical isolate 23 was susceptible to all four antibiotics (ciprofloxacin, cefazolin, ampicillin, and nitrofurantoin), whereas isolates 45 and 47 demonstrated resistance to ciprofloxacin (Table 2). *E. coli* clinical isolates 36, 97, 98 were resistant to ciprofloxacin, cefazolin, and ampicillin (Table 2). ASU2060 inhibited all six *E. coli* clinical isolates with a MIC of 8 verifying ASU2060 antimicrobial activity against clinically-relevant and multidrug-resistant *E. coli* strains (Table 2).

TABLE 2

ASU2060 inhibits antibiotic-resistant *E. coli* clinical isolates.

| E. coli clinical isolate | ciprofloxacin 2 μg/ml | ampicillin ≤8 μg/ml | cefazolin ≤16 μg/ml | nitrofurantoin 64 μg/ml | ASU2060 MIC (μM) |
|---|---|---|---|---|---|
| 23 | S | S | S | S | 8 |
| 45 | R | S | S | S | 8 |
| 47 | R | S | S | S | 8 |
| 36 | R | R | R | S | 8 |
| 97 | R | R | R | S | 8 |
| 98 | R | R | R | S | 8 |

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. An antimicrobial composition comprising at least one peptide selected from the group consisting of: ASU2001 (SEQ ID NO: 1), ASU2009 (SEQ ID NO:2), ASU2019 (SEQ ID NO: 3), ASU2056 (SEQ ID NO: 4), ASU2059 (SEQ ID NO: 5), and ASU2060 (SEQ ID NO: 6).

2. The composition of claim 1, further comprising a chelator that sequesters metal ions.

3. The composition of claim 2, wherein the chelator is EDTA.

4. The composition of claim 1, further comprising an antibiotic.

5. A method of treating a bacterial infection in a subject, the method comprising administering to the subject at least one peptide selected from the group consisting of: ASU2001 (SEQ ID NO: 1), ASU2009 (SEQ ID NO:2), ASU2019 (SEQ ID NO: 3), ASU2056 (SEQ ID NO: 4), ASU2059 (SEQ ID NO: 5), and ASU2060 (SEQ ID NO: 6).

6. The method of claim 5, wherein the bacterial infection is caused by a bacteria selected from the group consisting of: *Escherichia coli, Pseudomonas aeruginosa*, methicillin-resistant *Staphylococcus aureus* (MRSA), and *Mycobacterium abscessus*.

7. The method of claim 6, wherein the bacterial infection is a *mycobacterium* infection.

8. The method of claim 7, wherein the bacterial infection is caused by a drug-resistant *mycobacterium*.

9. The method of claim 8, wherein the *mycobacterium* infection is caused by *Mycobacterium abscessus*.

10. The method of claim 9, wherein the *M. abscessus* has a smooth morphotype.

11. The method of claim 10, wherein the at least one peptide is selected from the group consisting of: ASU2056 (SEQ ID NO: 4) and ASU2060 (SEQ ID NO: 6), the method further comprising administering to the subject a chelator that sequesters metal ions.

12. The method of claim 11, wherein the chelator is EDTA.

13. The method of claim 9, wherein the *M. abscessus* has a rough morphotype.

14. The method of claim 13, wherein the method consists of administering to the subject ASU2001 (SEQ ID NO: 1).

* * * * *

```
                         SEQUENCE LISTING

<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (14)..(17)
<223> OTHER INFORMATION: D-amino acid

<400> SEQUENCE: 1

Gln Phe Asn Gly Arg Ser Lys Ala Ala Lys Val Asn Phe Trp Arg Lys
1               5                   10                  15

Ala

<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (4)..(4)
<223> OTHER INFORMATION: D-amino acid
```

```
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (8)..(8)
<223> OTHER INFORMATION: D-amino acid
<220> FEATURE:
<221> NAME/KEY: MISC_FEATURE
<222> LOCATION: (9)..(9)
<223> OTHER INFORMATION: D-amino acid
<220> FEATURE:
<221> NAME/KEY: MISC_FEATURE
<222> LOCATION: (14)..(17)
<223> OTHER INFORMATION: D-amino acid

<400> SEQUENCE: 2

Arg Tyr Gly Leu Ser Lys Ala Arg Lys Val Asn Gln Phe Arg Lys Ala
1               5                   10                  15

Leu

<210> SEQ ID NO 3
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (12)..(14)
<223> OTHER INFORMATION: D-amino acid
<220> FEATURE:
<221> NAME/KEY: MISC_FEATURE
<222> LOCATION: (16)..(17)
<223> OTHER INFORMATION: D-amino acid

<400> SEQUENCE: 3

Arg Val Gly Pro Ser Ala Pro His Asn Leu Phe Arg Arg Lys Ser Ala
1               5                   10                  15

Leu

<210> SEQ ID NO 4
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-amino acid
<220> FEATURE:
<221> NAME/KEY: MISC_FEATURE
<222> LOCATION: (5)..(5)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (11)..(11)
<223> OTHER INFORMATION: D-amino acid
<220> FEATURE:
```

```
<221> NAME/KEY: MISC_FEATURE
<222> LOCATION: (14)..(16)
<223> OTHER INFORMATION: D-amino acid

<400> SEQUENCE: 4

Gln Arg Trp Gly Leu Ser Leu Ala Pro Tyr Lys Asn Phe Arg Arg Leu
1               5                   10                  15
Ser

<210> SEQ ID NO 5
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (9)..(12)
<223> OTHER INFORMATION: D-amino acid
<220> FEATURE:
<221> NAME/KEY: MISC_FEATURE
<222> LOCATION: (14)..(15)
<223> OTHER INFORMATION: D-amino acid

<400> SEQUENCE: 5

Tyr Gly Arg Ser Ala Arg Tyr Asn Arg Arg Lys Leu Gly Ala Leu Ser
1               5                   10                  15
Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-amino acid
<220> FEATURE:
<221> NAME/KEY: MISC_FEATURE
<222> LOCATION: (7)..(7)
<223> OTHER INFORMATION: D-amino acid
<220> FEATURE:
<221> NAME/KEY: MISC_FEATURE
<222> LOCATION: (11)..(14)
<223> OTHER INFORMATION: D-amino acid
<220> FEATURE:
<221> NAME/KEY: MISC_FEATURE
<222> LOCATION: (17)..(17)
<223> OTHER INFORMATION: D-amino acid

<400> SEQUENCE: 6

Val Gly Arg Trp Ser Ala Arg Tyr Asn Phe Arg Trp Arg Lys Ser Gly
1               5                   10                  15
Leu
```